US010182877B2

(12) United States Patent
Marshburn

(10) Patent No.: US 10,182,877 B2
(45) Date of Patent: Jan. 22, 2019

(54) SURGICAL DRAPE FOR COLLECTING DISCHARGED FLUID

(71) Applicant: The Charlotte-Mecklenburg Hospital Authority, Charlotte, NC (US)

(72) Inventor: Paul B. Marshburn, Davidson, NC (US)

(73) Assignee: The Charlotte-Mecklenburg Hospital Authority, Charlotte, NC (US)

(*) Notice: Subject to any disclaimer, the term of this patent is extended or adjusted under 35 U.S.C. 154(b) by 362 days.

(21) Appl. No.: 14/892,128

(22) PCT Filed: May 30, 2014

(86) PCT No.: PCT/US2014/040193
§ 371 (c)(1),
(2) Date: Nov. 18, 2015

(87) PCT Pub. No.: WO2014/197306
PCT Pub. Date: Dec. 11, 2014

(65) Prior Publication Data
US 2016/0081751 A1 Mar. 24, 2016

Related U.S. Application Data

(60) Provisional application No. 61/828,904, filed on May 30, 2013, provisional application No. 61/924,898, filed on Jan. 8, 2014.

(51) Int. Cl.
*A61B 46/00* (2016.01)
*A61B 19/08* (2006.01)
(Continued)

(52) U.S. Cl.
CPC ............ *A61B 46/30* (2016.02); *A61B 19/087* (2013.01); *A61B 46/00* (2016.02);
(Continued)

(58) Field of Classification Search
CPC . A61B 46/30; A61B 19/087; A61B 2046/205; A61B 2019/463;
(Continued)

(56) References Cited

U.S. PATENT DOCUMENTS 3,494,356 A * 2/1970 Melges ................. A61B 46/30
128/849
3,589,365 A * 6/1971 Sejman ................. A61B 46/30
128/849
(Continued)

FOREIGN PATENT DOCUMENTS

GB 1500009 2/1978

OTHER PUBLICATIONS

Allahbadia et al., Hysteroscopic fallopian tube recanalization using a flexible guide cannula and hydrophilic guide wire, Gynaecological Endoscopy, 2000, pp. 31-35, vol. 9.
(Continued)

*Primary Examiner* — Tarla R Patel
(74) *Attorney, Agent, or Firm* — Myers Bigel, P.A.

(57) ABSTRACT

A surgical drape (100) is described that is aimed at providing a way to direct a maximum amount of fluid (e.g., distention fluid) discharged from the patient's uterine cavity to a collection point, such as a fluid management system, during a hysteroscopic procedure. The surgical drape may include a cover portion (105) and a collection portion (110) that is attached to the cover portion (105). The cover portion (105) may define an opening (115) that provides a surgeon with surgical access to the patient for performing a medical procedure. The collection portion (110) may include a main panel (120) that can be attached to the patient's back distally of the gluteal cleft (e.g., via an adhesive strip). The main panel (110) may include a pocket (170), via which the
(Continued)

surgeon may insert his hands to position the main panel (110) under the patient without disturbing the sterile field.

23 Claims, 19 Drawing Sheets

(51) Int. Cl.
| | | |
|---|---|---|
| A61B 46/23 | (2016.01) | |
| A61B 90/00 | (2016.01) | |
| A61B 19/10 | (2006.01) | |
| A61B 19/00 | (2006.01) | |
| A61B 46/20 | (2016.01) | |

(52) U.S. Cl.
CPC ... *A61B 2019/085* (2013.01); *A61B 2019/106* (2013.01); *A61B 2019/463* (2013.01); *A61B 2046/205* (2016.02); *A61B 2046/236* (2016.02); *A61B 2090/063* (2016.02)

(58) Field of Classification Search
CPC ........ A61B 2019/106; A61B 2019/085; A61B 2046/236; A61B 2090/063; A61B 46/00; A61B 46/40
See application file for complete search history.

(56) References Cited

U.S. PATENT DOCUMENTS

| | | | |
|---|---|---|---|
| 3,693,618 A | 9/1972 | Madden | |
| 5,143,091 A * | 9/1992 | Patnode | A61B 46/00 128/849 |
| 5,395,354 A | 3/1995 | Vancaillie | |
| 5,709,221 A | 1/1998 | Vancaillie et al. | |
| 5,947,122 A | 9/1999 | McDonald et al. | |
| 6,070,586 A * | 6/2000 | Harroll | A61B 46/20 128/849 |
| 6,213,124 B1 | 4/2001 | Butterworth | |
| 6,938,639 B1 | 9/2005 | Robinson | |
| 7,305,991 B2 * | 12/2007 | Santilli | A61B 50/30 128/849 |
| 7,690,380 B2 * | 4/2010 | Lee | A61B 46/27 128/849 |
| 2002/0092563 A1 | 7/2002 | Robinson | |
| 2004/0118409 A1 | 6/2004 | Griesbach, III | |
| 2005/0022822 A1 | 2/2005 | Santilli et al. | |
| 2005/0133092 A1 | 6/2005 | Robinson | |
| 2007/0023053 A1 * | 2/2007 | Bowen | A61B 46/30 128/853 |
| 2007/0135784 A1 | 6/2007 | Tankersley | |
| 2008/0168995 A1 | 7/2008 | Yardan et al. | |
| 2010/0175700 A1 * | 7/2010 | West | A61B 46/30 128/851 |
| 2011/0174318 A1 | 7/2011 | Reyes et al. | |
| 2012/0222686 A1 | 9/2012 | Lockwood et al. | |

OTHER PUBLICATIONS

International Search Report for corresponding PCT Application No. PCT/US2014/040193, dated Sep. 26, 2014, 5 pages.

\* cited by examiner

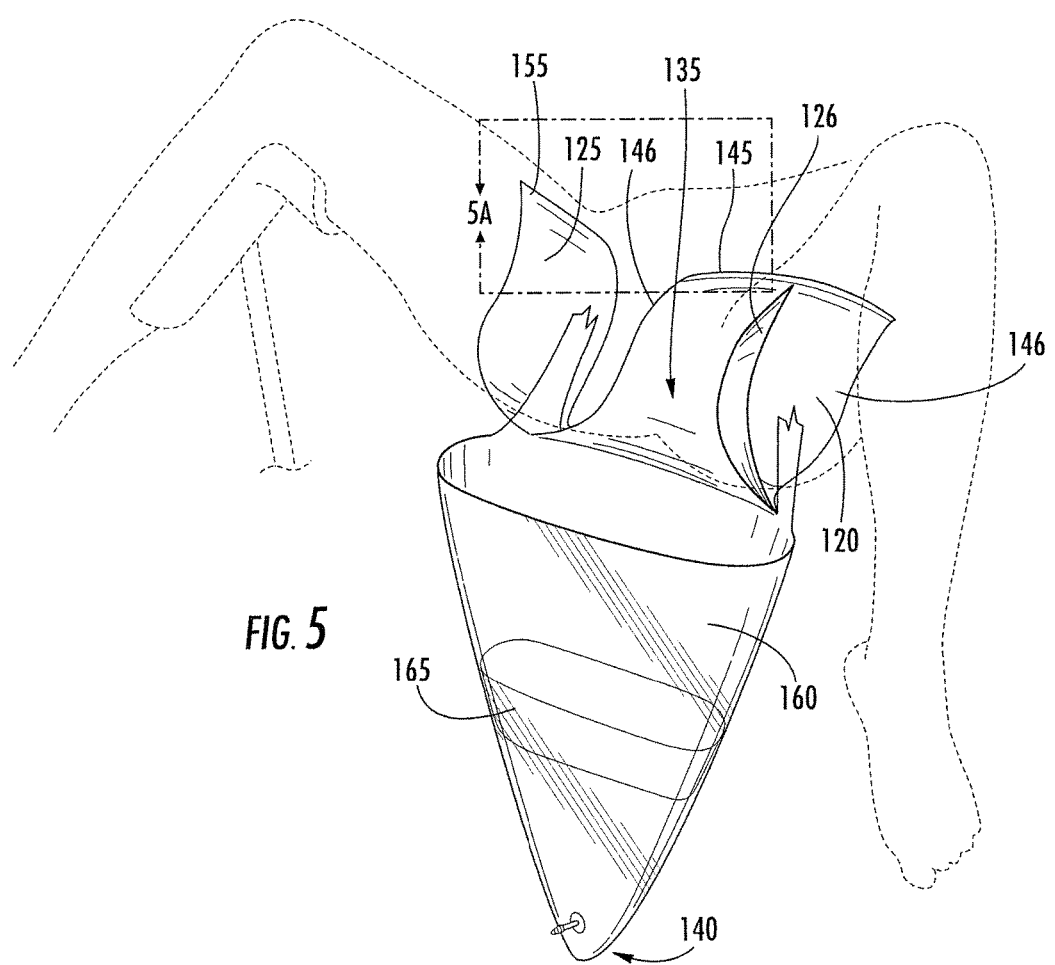

SURGICAL DRAPE FOR COLLECTING DISCHARGED FLUID

FIELD OF THE INVENTION

The present invention relates generally to surgical drapes used in medical procedures in which fluid that is discharged from the patient is to be collected, such as in hysteroscopic procedures.

BACKGROUND

In certain medical procedures in which a body cavity is inspected, distention fluid may be used to facilitate the examination. For example, during a hysteroscopic procedure, which may be used to treat various types of intra-uterine abnormalities such as menorrhagia, uterine polyps, fibroids, etc., the uterine cavity may be inspected using endoscopy via the patient's cervix. Such a procedure typically involves passing a hysteroscope transvaginally through a dilated cervix and into the uterine cavity. The cavity may then be distended to allow for proper inspection by introducing a fluid or gas into the cavity to expand the cavity.

In cases in which a distending fluid, such as an electrolytic solution (e.g., saline) or non-electrolytic solution (e.g., glucose, glycine, etc.) is used to insufflate the uterine cavity, there may be a risk of fluid overload and intoxication of the patient as a result of over-absorption of the fluid through the uterine wall. The amount of fluid absorbed by the patient during the procedure depends on the patient's anatomy and metabolism, as well as the duration of the procedure.

Accordingly, there is a need for surgical drapes and methods for facilitating the accurate monitoring of fluid absorption by the patient during a medical procedure such as a hysteroscopy. Accurate fluid monitoring may allow a surgeon to have the maximum amount of time to perform and complete the procedure while ensuring a safe and effective outcome for the patient.

BRIEF SUMMARY OF EXAMPLE EMBODIMENTS

Accordingly, embodiments of surgical drapes and methods for collecting fluids discharged from a patient cavity, such as during a hysteroscopic procedure, are provided. The surgical drape may include a cover portion defining an opening configured to provide surgical access to a patient and a collection portion attached to the cover portion. The collection portion may comprise a main panel extending between two side panels. The main panel may be configured to be disposed under the patient's buttocks in a first nominal plane, and each side panel may be arranged in a second nominal plane that is at an angle with respect to the first nominal plane so as to form a trough for directing fluid discharged from the patient to a collection point.

In some cases, a distal edge of the main panel may be configured to be attached to an underside of the patient's body distally of the gluteal cleft. The distal edge of the main panel may comprise an adhesive strip. At least a portion of a lateral edge of each side panel may be configured to be attached to a corresponding thigh of the patient and may, in some cases, comprise an adhesive strip.

In some embodiments, the collection portion may define a distal edge. The distal edge of the collection portion may be configured to be attached to the patient's body such that the trough surrounds the patient's gluteal cleft and at least a portion of the patient's buttocks. Additionally or alternatively, the collection point may comprise a collection pouch configured to direct the fluid discharged from the patient to a collection system for measuring a volume of the fluid. The collection portion may be integrally formed with the collection pouch. Moreover, the collection portion may be attached to the cover portion via the collection pouch. The collection portion may comprise a plastic material, and the fluid discharged from the patient may comprise distention fluid.

In other embodiments, a method of monitoring a distention fluid deficit level in a patient undergoing a hysteroscopy is provided. According to embodiments of the method, the patient is positioned in a lithotomy position, and a surgical drape is placed over the patient. The surgical drape may comprise a cover portion defining an opening and a collection portion attached to the cover portion. The surgical drape may be arranged such that the cover portion covers the patient's body and the opening is positioned to provide surgical access to the patient's pelvic region. A main panel of the collection portion may be disposed under the patient's buttocks in a first nominal plane. In addition, each of two side panels of the collection portion that extend from the main panel may be arranged such that each side panel is in a second nominal plane that is at an angle with respect to the first nominal plane so as to form a trough for directing distention fluid discharged from the patient to a collection point.

In some cases, disposing the main panel may include attaching a distal edge of the main panel to an underside of the patient's body distally of the gluteal cleft. Furthermore, arranging each of the two side panels may include attaching at least a portion of a lateral edge of each side panel to a corresponding thigh of the patient. Additionally or alternatively, the distention fluid may be collected at the collection point via a collection pouch and directed to a collection system for measuring a volume of the fluid.

In still other embodiments, a method of manufacturing a surgical drape may be provided. The method may include defining an opening in a cover portion, wherein the opening is configured to provide surgical access to a patient. The method may further include forming a collection portion comprising a main panel extending between two side panels and attaching the collection portion to the cover portion at first and second connection interfaces. The main panel may be configured to be disposed under the patient's buttocks in a first nominal plane, and each side panel may be configured to be arranged in a second nominal plane that is at an angle with respect to the first nominal plane so as to form a trough for directing fluid discharged from the patient to a collection point.

In some cases, an adhesive strip may be disposed on a distal edge of the main panel such that the adhesive strip is configured to attach the distal edge of the main panel to the underside of the patient's body distally of the gluteal cleft. Furthermore, an adhesive strip may be disposed on at least a portion of the lateral edge of each side panel such that the adhesive strip is configured to attach the respective portion to the patient's body. In some embodiments, a collection pouch may be provided proximate the collection point. The collection pouch may be configured to direct the fluid to a collection system for measuring a volume of the fluid. The collection pouch may be integral to at least one of the main panel or the side panels of the collection portion.

In still other embodiments, a surgical drape may be provided that includes a cover portion defining an opening configured to provide surgical access to a patient and a collection portion attached to the cover portion. The collection portion may comprise a collection pouch and a main panel extending from the collection pouch. The main panel may be configured to be disposed under the patient's buttocks so as to direct fluid discharged from the patient to a collection point via the collection pouch.

In some cases, a distal edge of the main panel may be configured to be attached to an underside of the patient's body distally of the gluteal cleft. At least a portion of each side edge of the main panel may be configured to be attached to a corresponding part of the patient's underside. The distal edge and the side edges of the main panel may, for example, comprise adhesive strips.

In some embodiments, the surgical drape may further comprise a barrier strip disposed proximate a distal edge of the main panel that is configured to urge the distal edge towards contact with the patient's body so as to reduce a flow of the fluid discharged from the patient distally with respect to the barrier strip.

In still other embodiments, a surgical drape is provided that includes a cover portion and a collection portion attached to the cover portion. The cover portion may define an opening configured to provide surgical access to a patient. The collection portion may comprise a collection pouch and a main panel extending from the collection pouch. The main panel may be configured to be disposed under the patient's buttocks so as to direct fluid discharged from the patient to a collection point via the collection pouch.

In some cases, a distal edge of the main panel may be configured to be attached to an underside of the patient's body distally of the gluteal cleft. The main panel may include side edges, between which the distal edge may extend, and at least a portion of each side edge of the main panel may be configured to be attached to a corresponding part of the patient's underside. The distal edge and the side edges of the main panel may comprise adhesive strips.

In some embodiments, the surgical drape may comprise a barrier strip disposed proximate a distal edge of the main panel configured to urge the distal edge towards contact with the patient's body so as to reduce a flow of the fluid discharged from the patient distally with respect to the barrier strip. Moreover, in some cases, the main panel may comprise a pocket configured to receive at least one hand of an operator for allowing the operator to position the collection portion while maintaining a sterile field. The cover portion may define a slit, and the pocket may be accessible via the slit. The slit may be defined proximate a lower edge of the opening of the cover portion. An upper edge of the slit may be connected to a corresponding rear edge of an opening of the collection pouch.

In some cases, the surgical drape may further comprise a reinforcing member disposed proximate an opening of the collection pouch and configured to urge the collection pouch to maintain an open configuration. The collection portion may be configured to collect distention fluid discharged from the patient.

In still other embodiments, a method of monitoring a distention fluid deficit level in a patient undergoing a hysteroscopy is provided that includes positioning the patient in a lithotomy position; placing a surgical drape over the patient, wherein the surgical drape comprises a cover portion defining an opening and a collection portion attached to the cover portion, such that the cover portion covers the patient's body and the opening is positioned to provide surgical access to the patient's pelvic region; and disposing a main panel of the collection portion under the patient's buttocks such that distention fluid discharged from the patient is collected via a collection pouch of the collection portion.

Disposing the main panel may, in some cases, comprise attaching a distal edge of the main panel to an underside of the patient's body distally of the gluteal cleft. Attaching the distal edge of the main panel may comprise accessing a pocket defined by the main panel, wherein the pocket is configured to maintain a sterile field. In some cases, the method may further comprise directing the distention fluid to a collection system for measuring a volume of the fluid.

In still other embodiments, a method of manufacturing a surgical drape is provided that comprises defining an opening in a cover portion, wherein the opening is configured to provide surgical access to a patient; and forming a collection portion comprising a main panel and a collection pouch configured to collect distention fluid discharged from the patient, where the main panel is configured to be disposed under the patient's buttocks so as to direct fluid discharged from the patient to the collection pouch.

In some cases, the method may further comprise disposing an adhesive strip on a distal edge of the main panel such that the adhesive strip is configured to attach the distal edge of the main panel to the underside of the patient's body distally of the gluteal cleft. The method may further comprise defining a slit in the cover portion proximate a lower edge of the opening of the cover portion and/or connecting an upper edge of the slit to a corresponding rear edge of an opening of the collection pouch. Additionally or alternatively, a reinforcing member may be provided proximate an opening of the collection pouch, wherein the reinforcing member is configured to urge the collection pouch to maintain an open configuration.

BRIEF DESCRIPTION OF THE DRAWINGS

Figure 1:
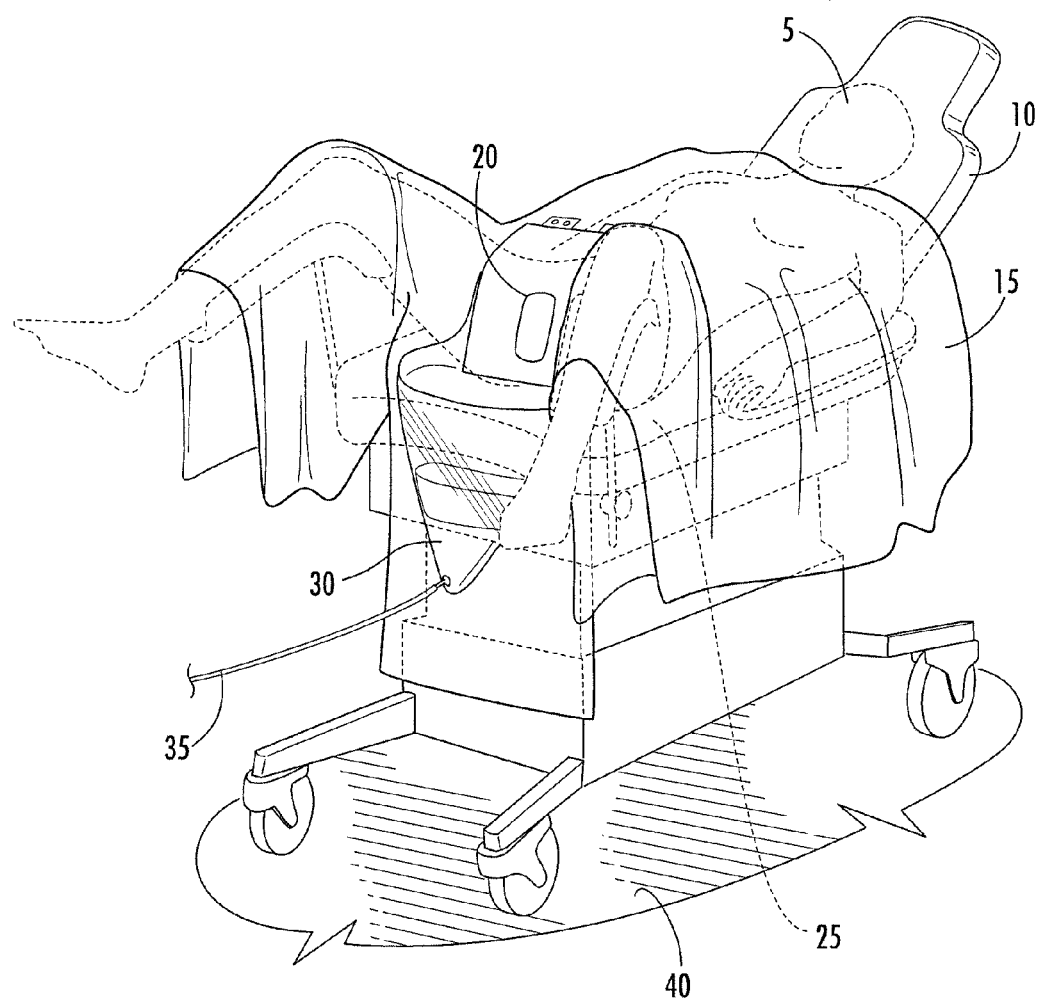
Figure 2:
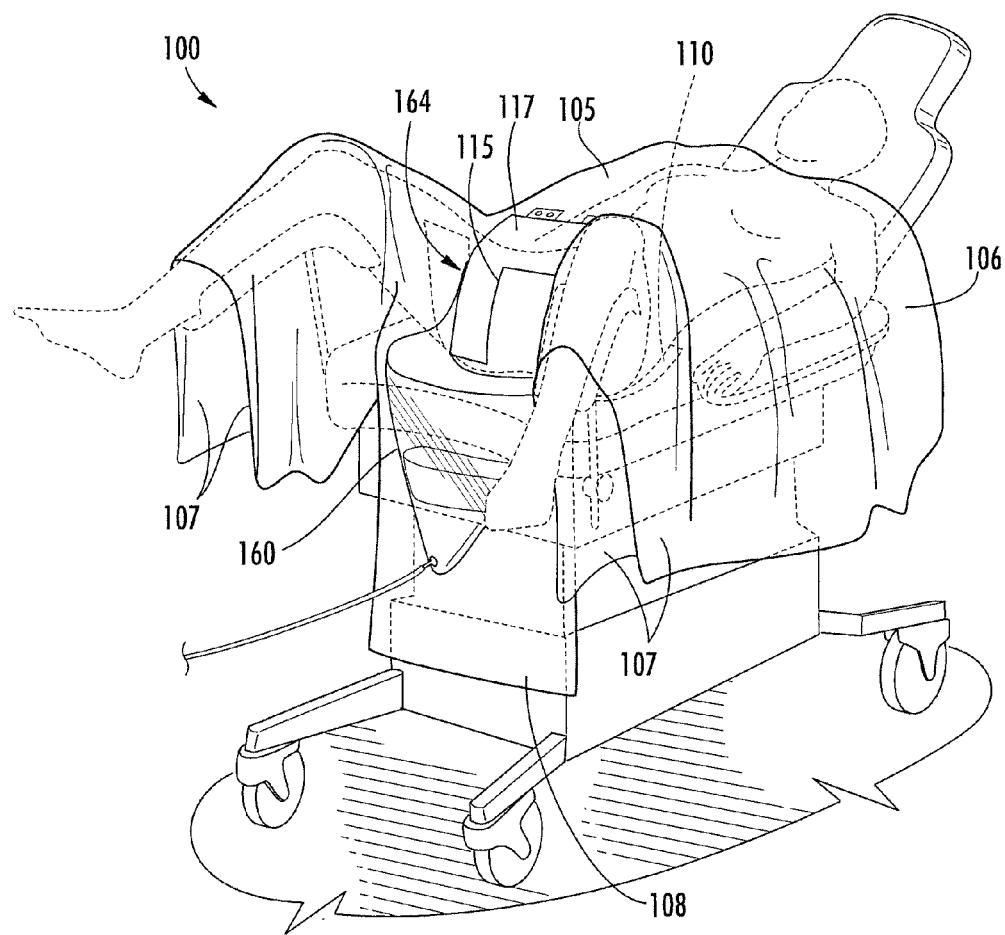
Figure 3:
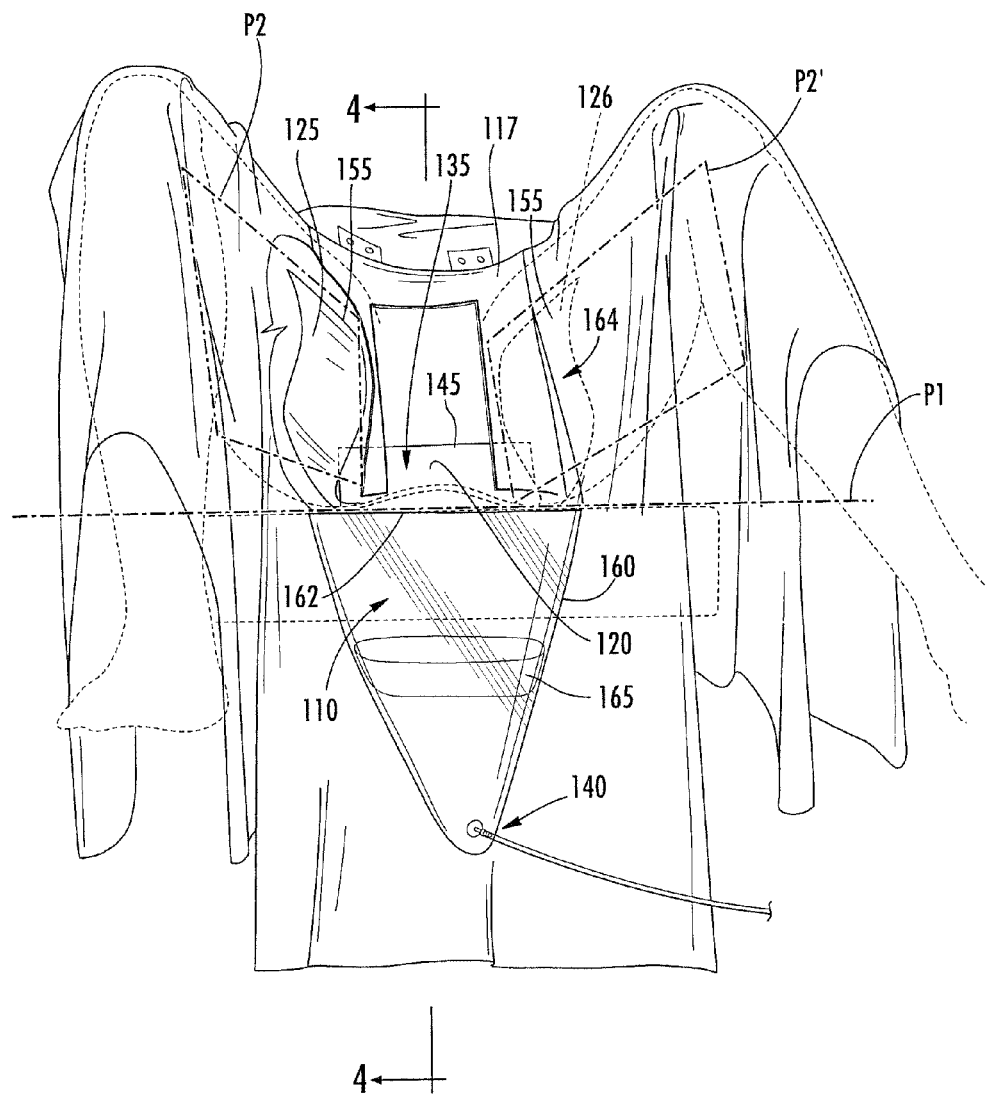
Figure 4:
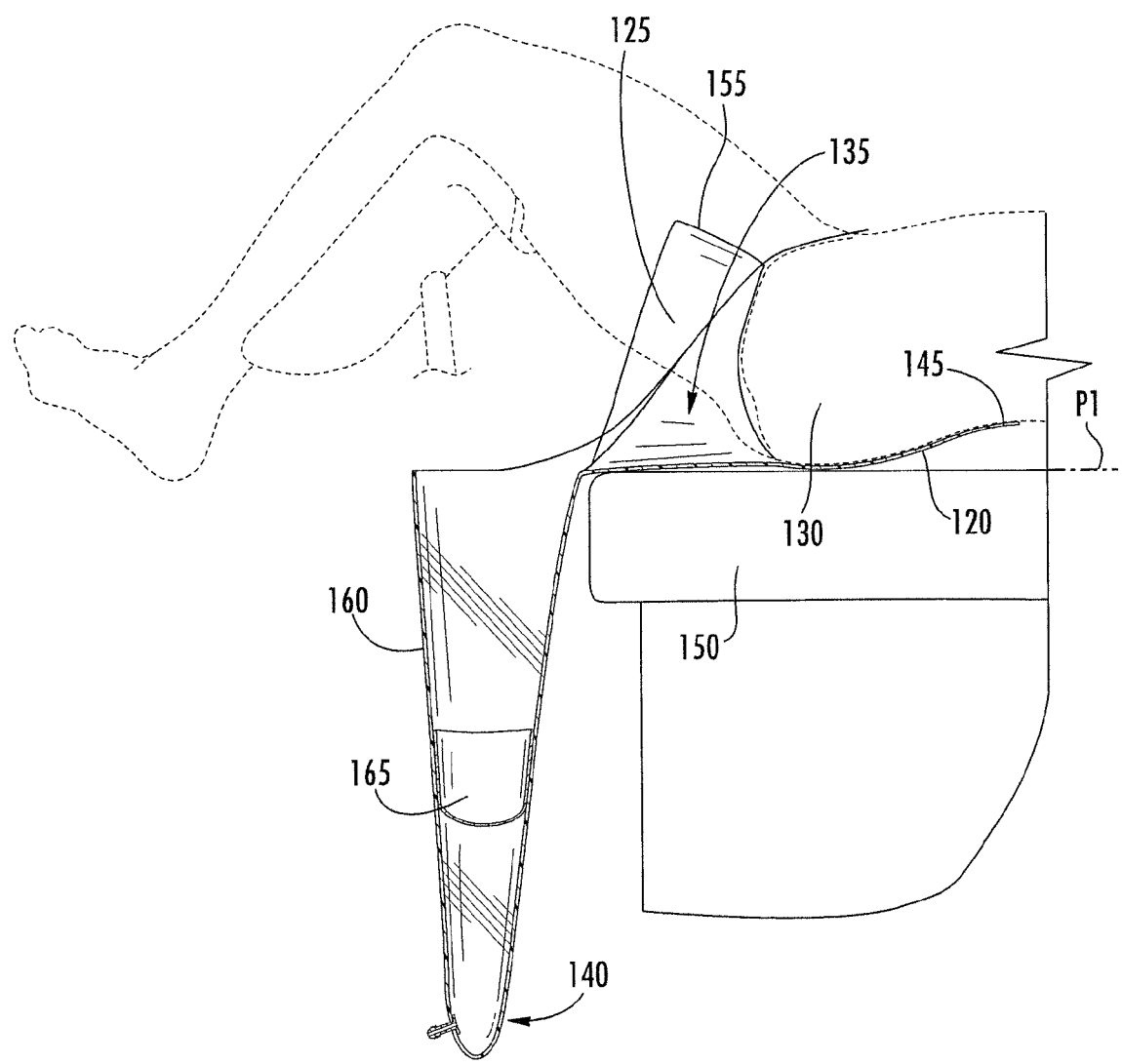
Figure 5A:
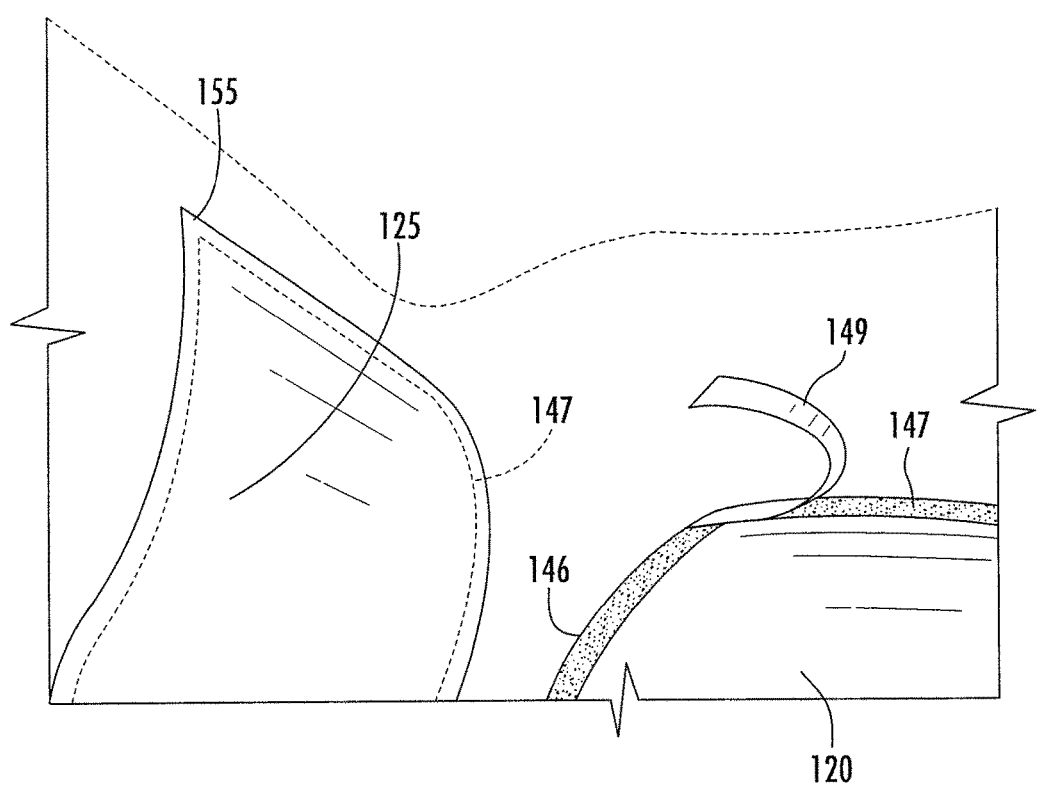
Figure 6:
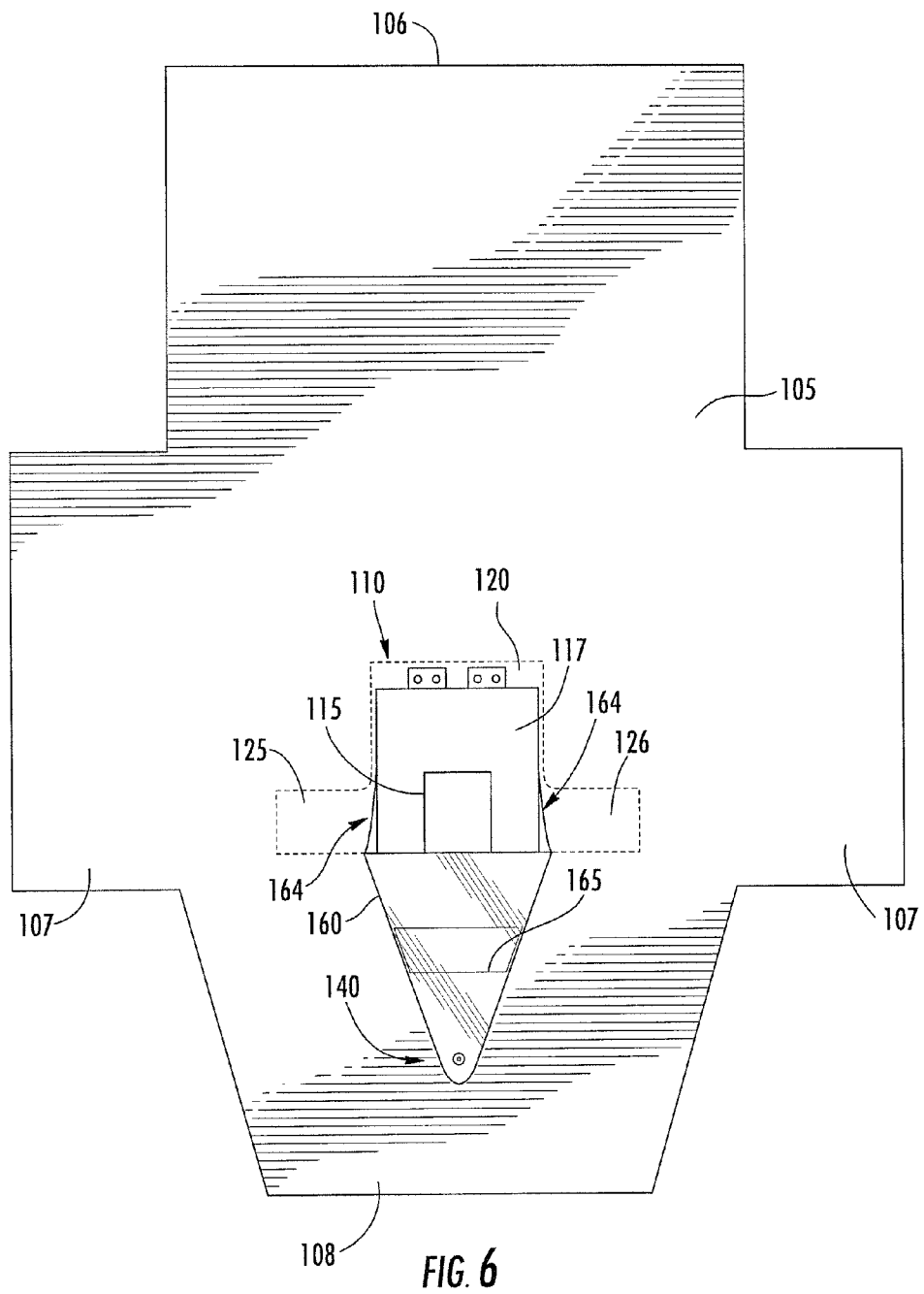
Figure 7:
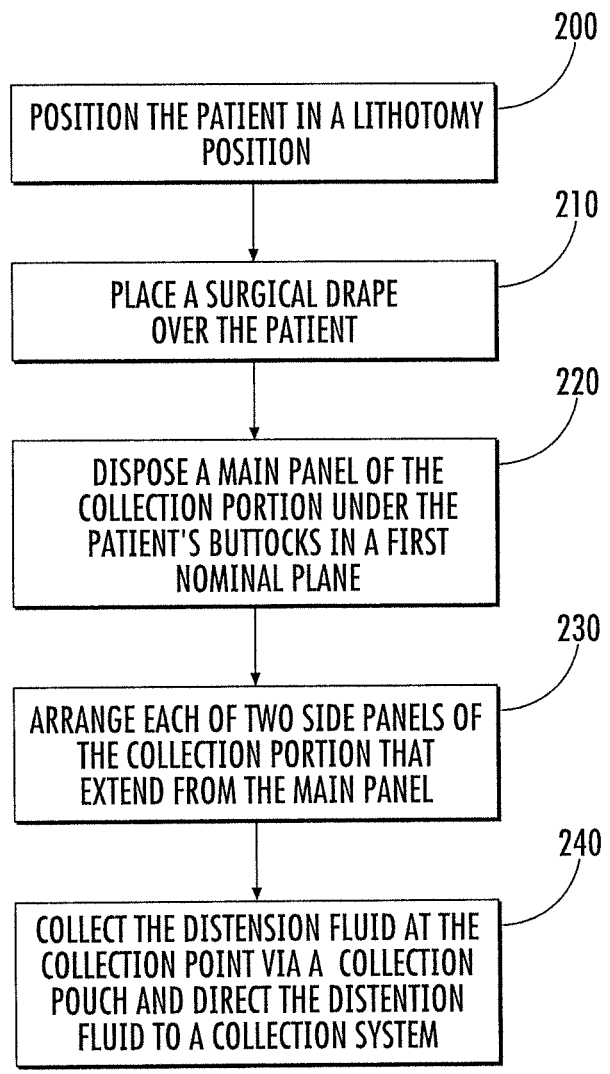
Figure 8:
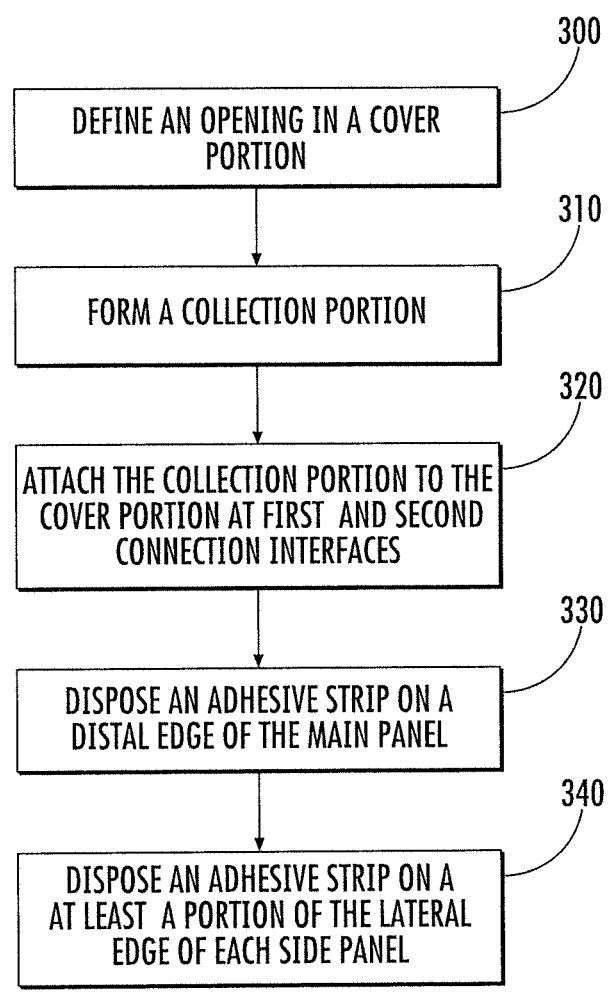
Figure 9:
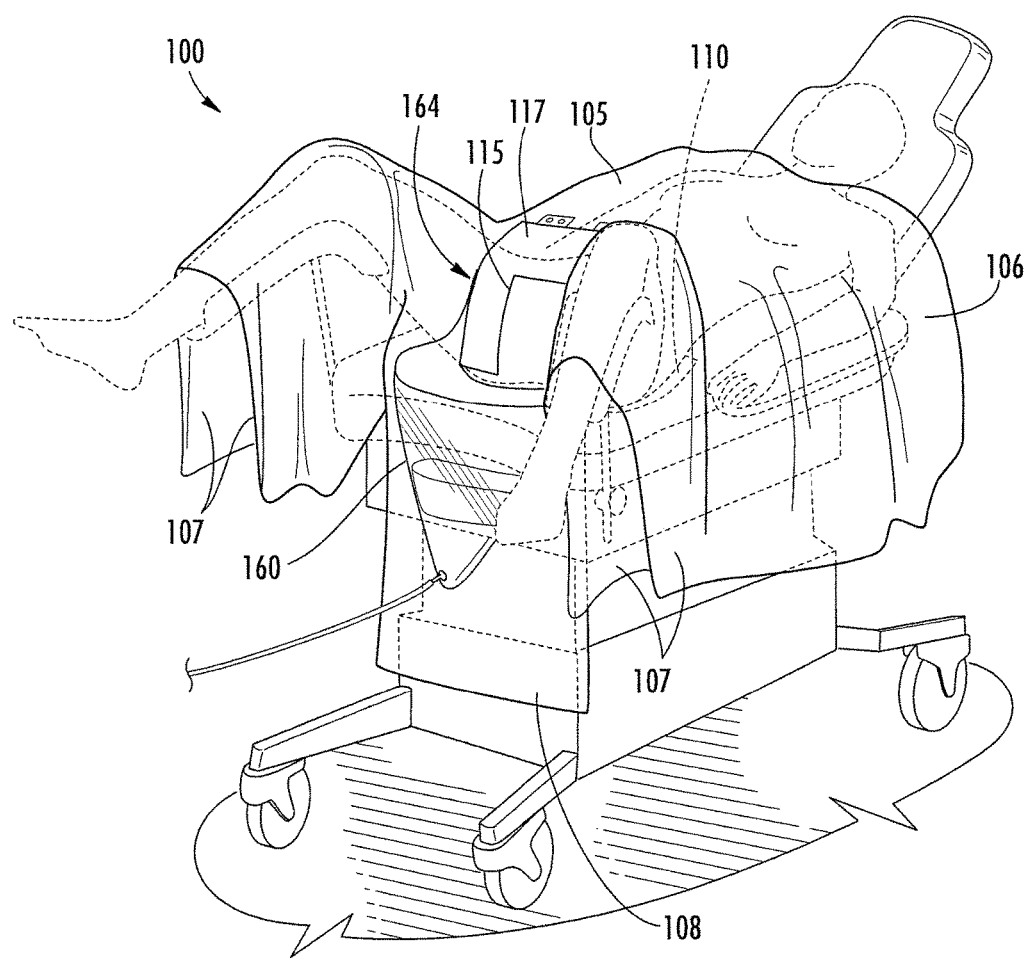
Figure 10:
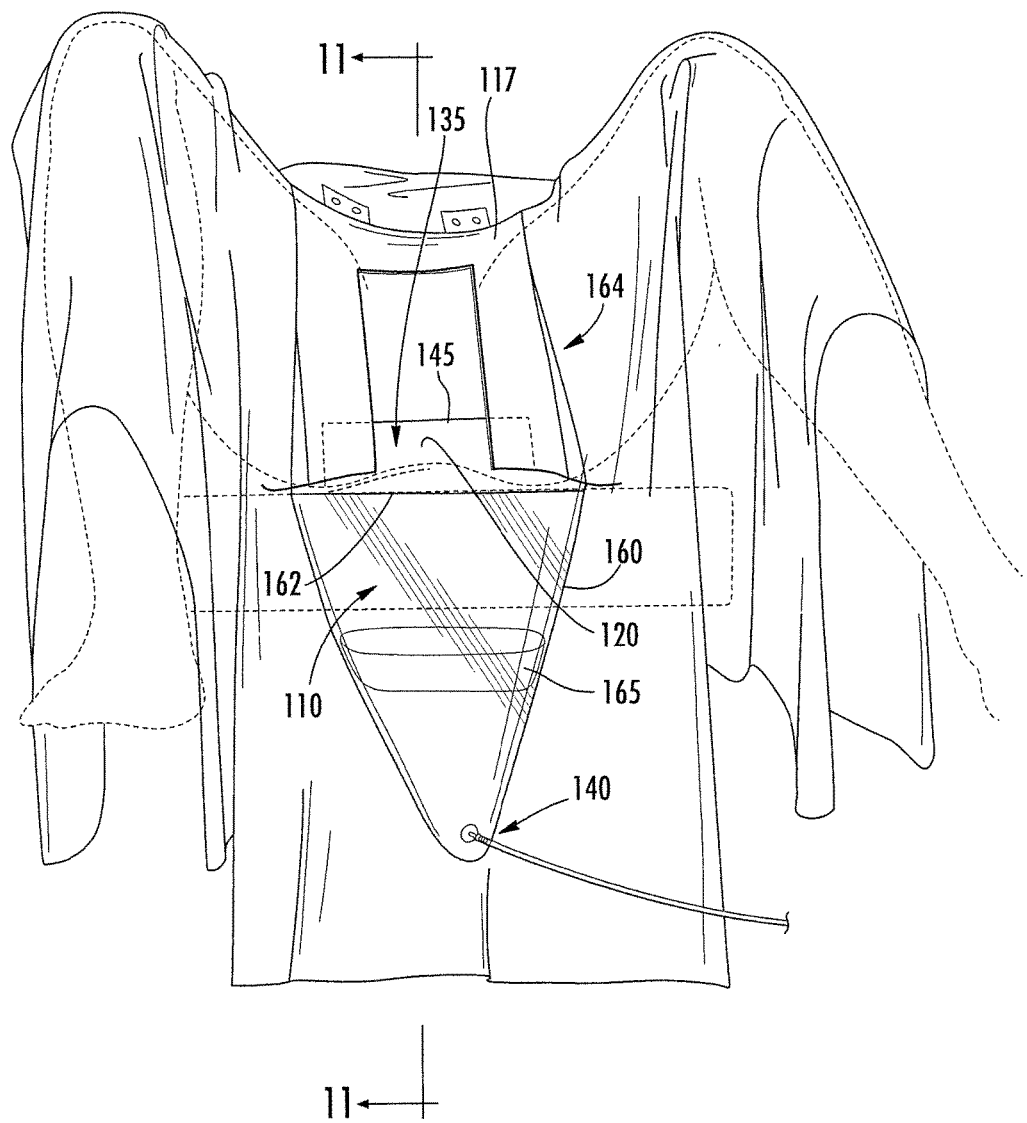
Figure 11:
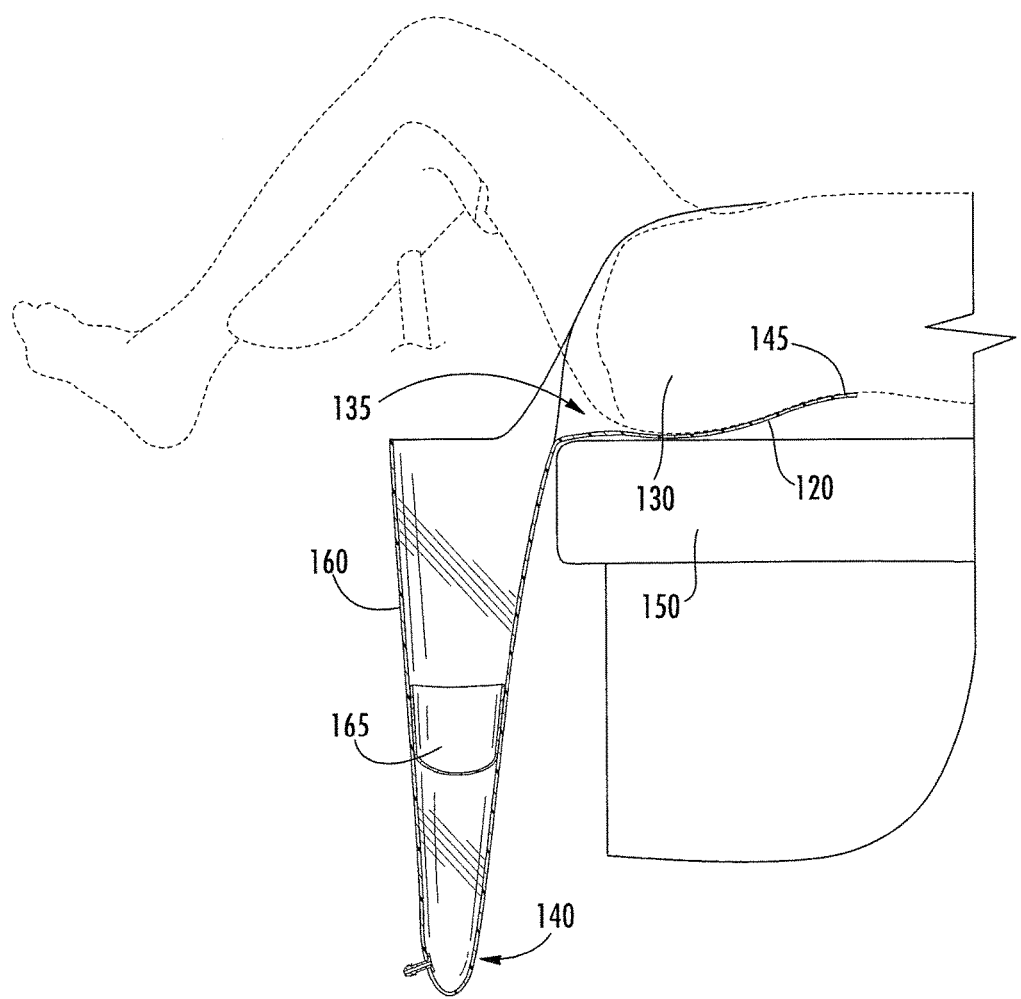
Figure 12:
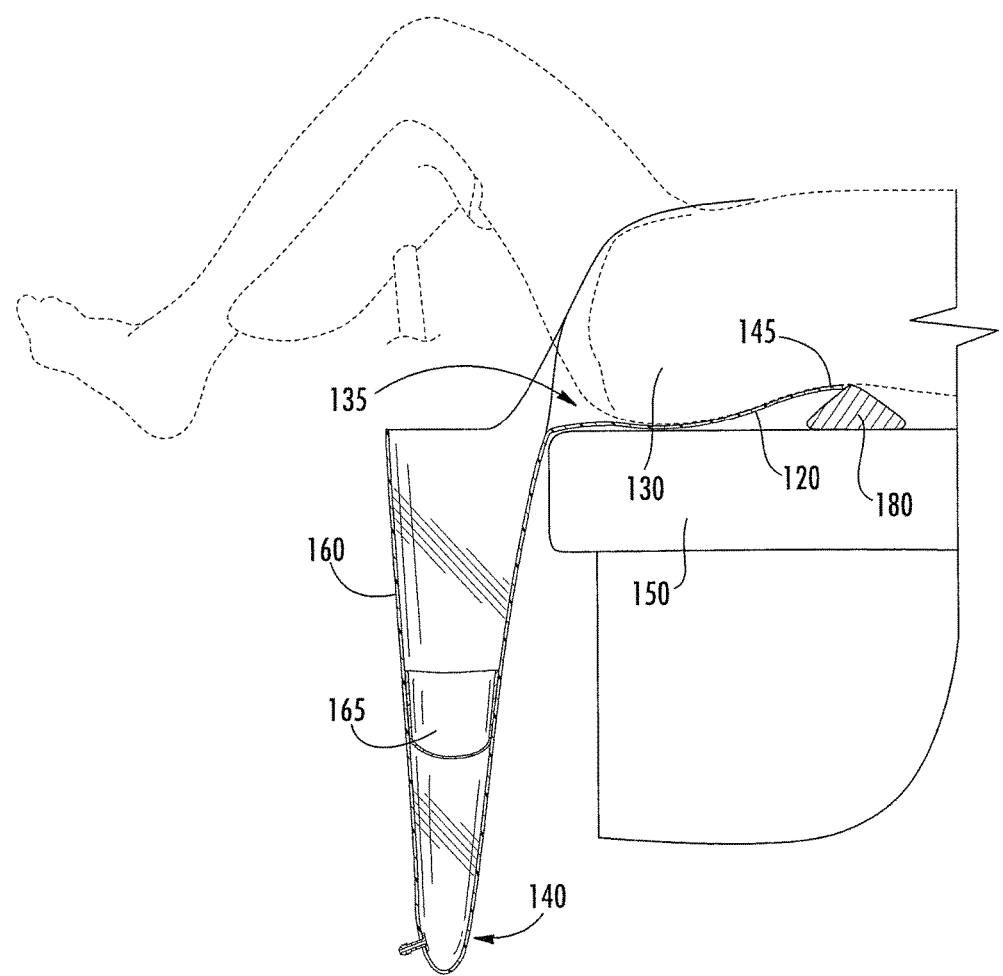
Figure 13:
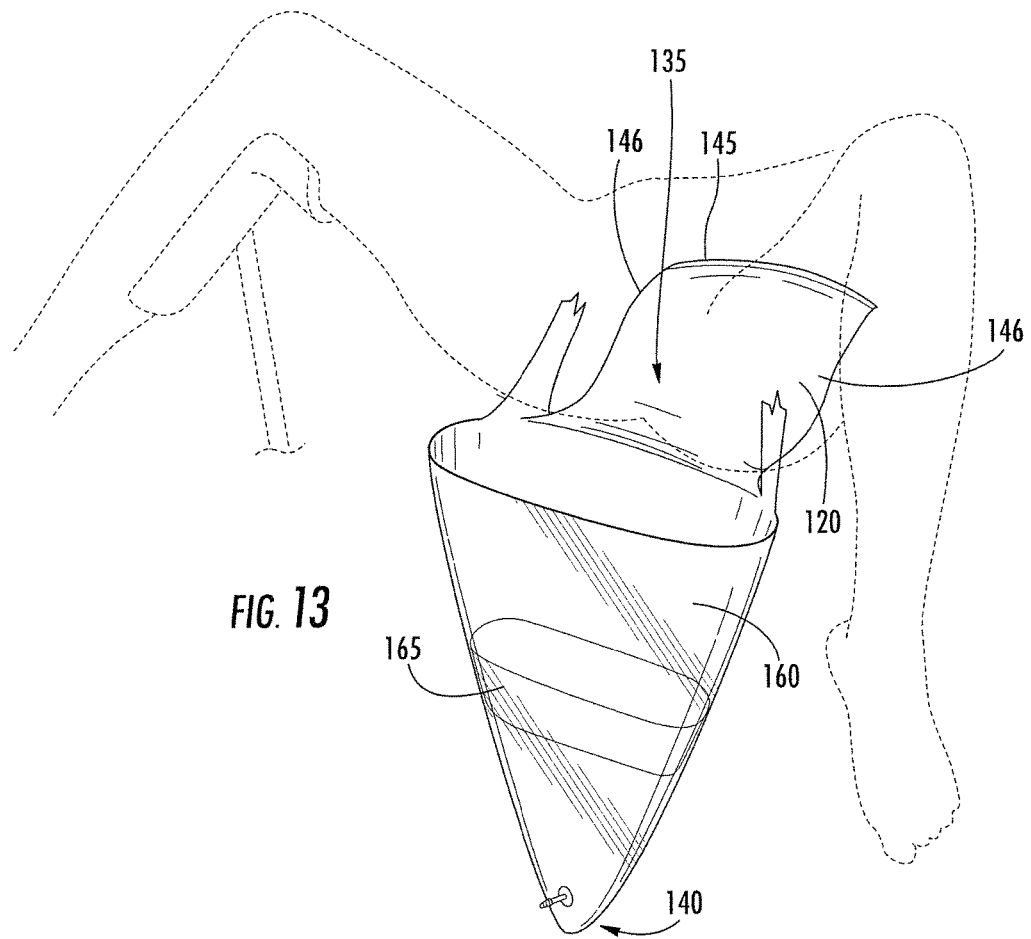
Figure 14:
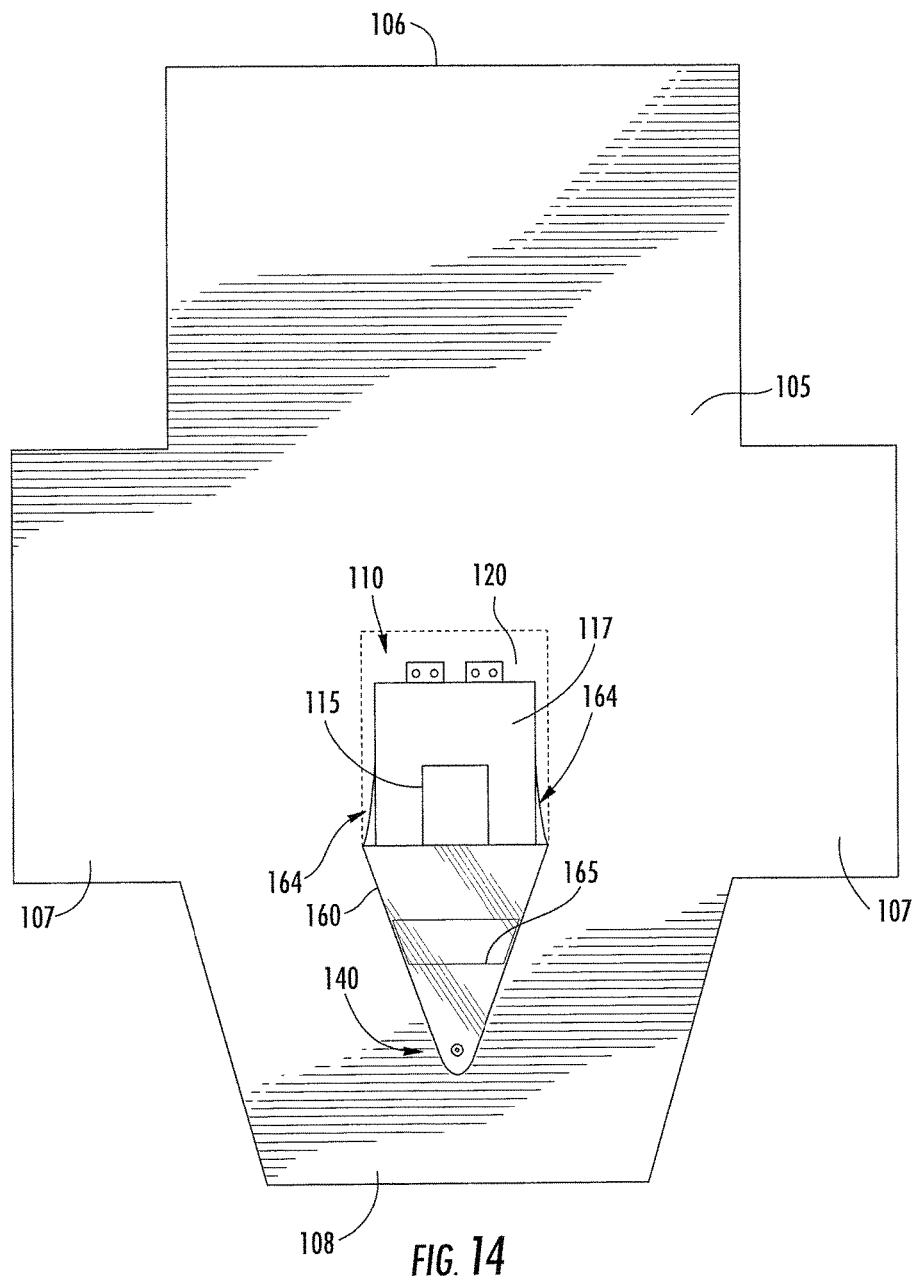
Figure 15A:
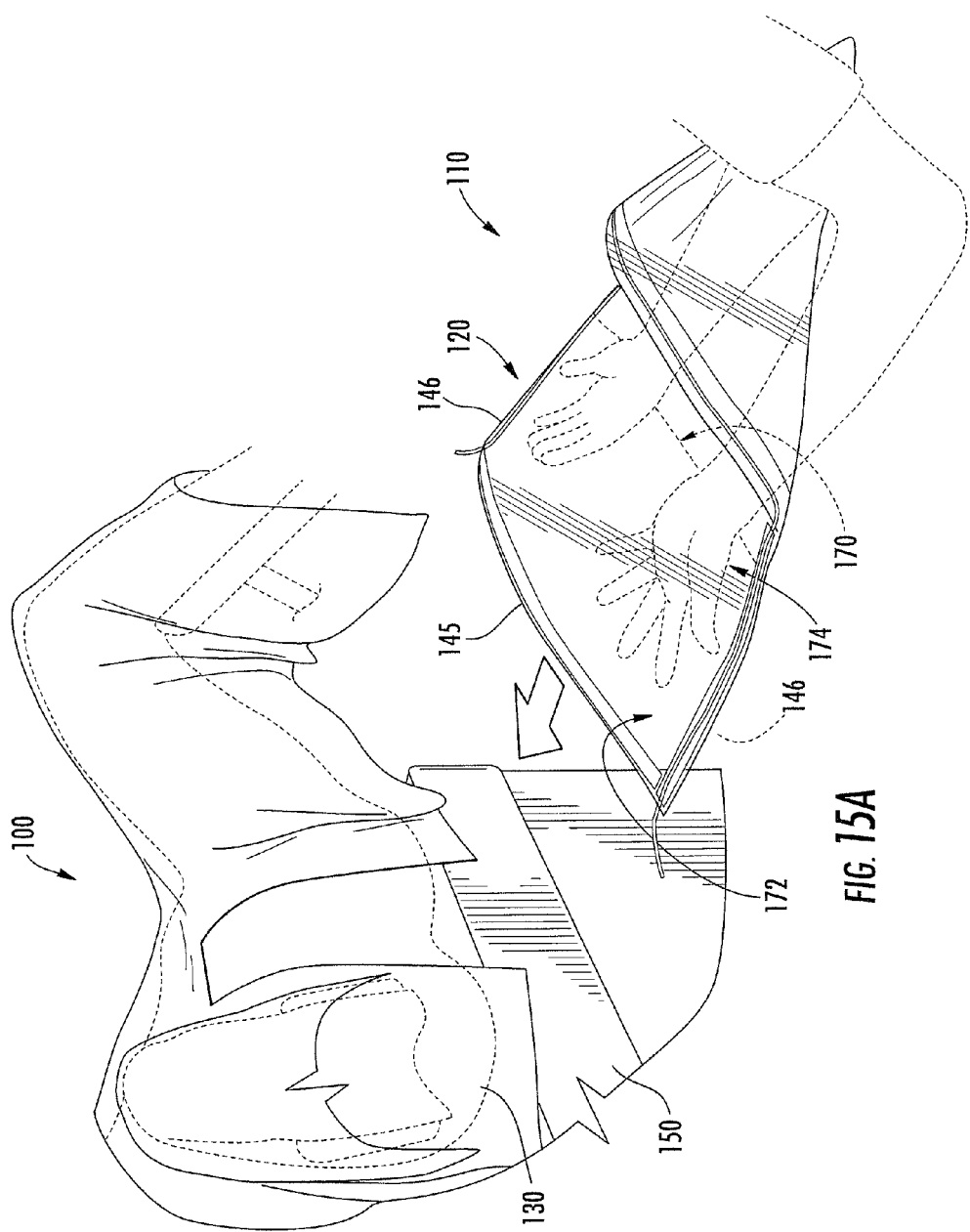
Figure 15B:
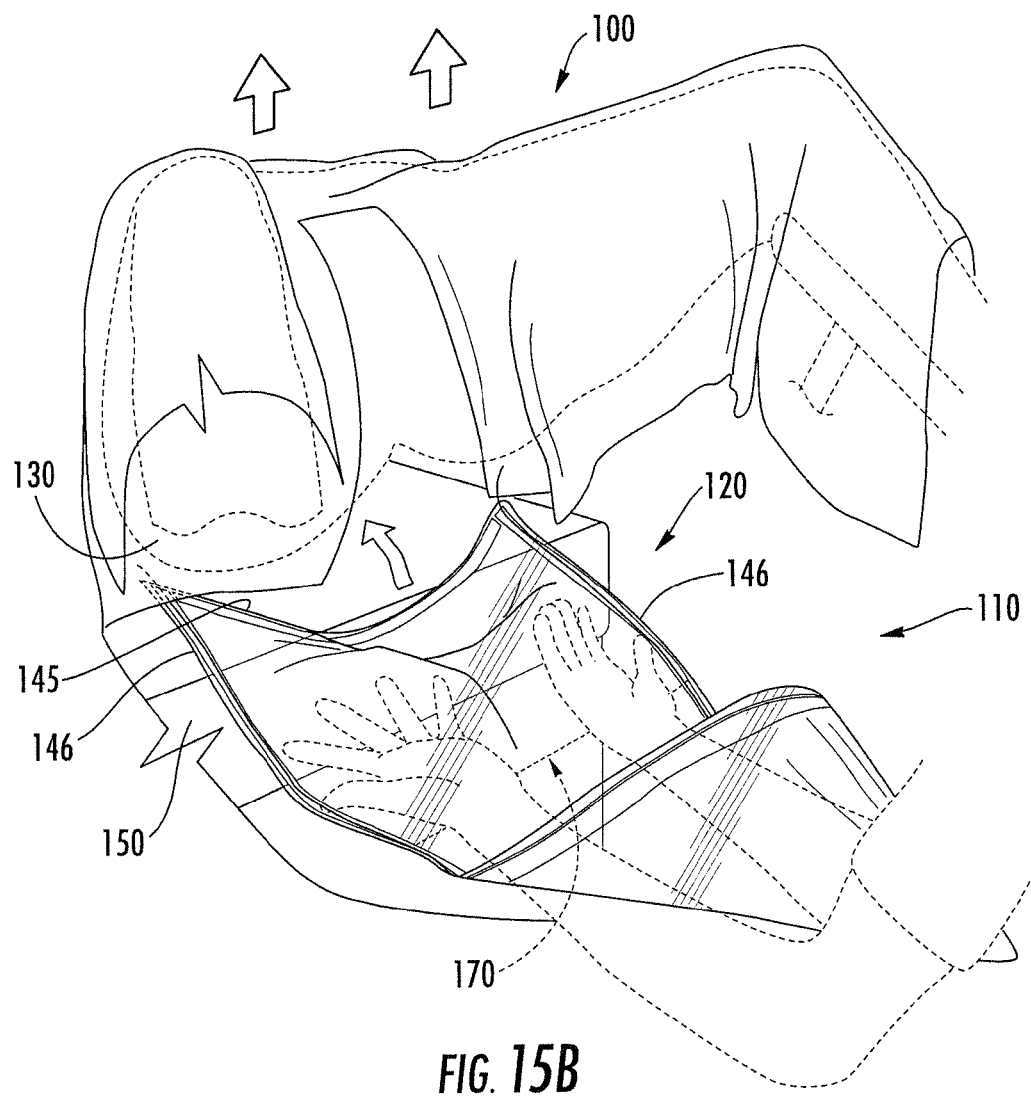
Figure 16:
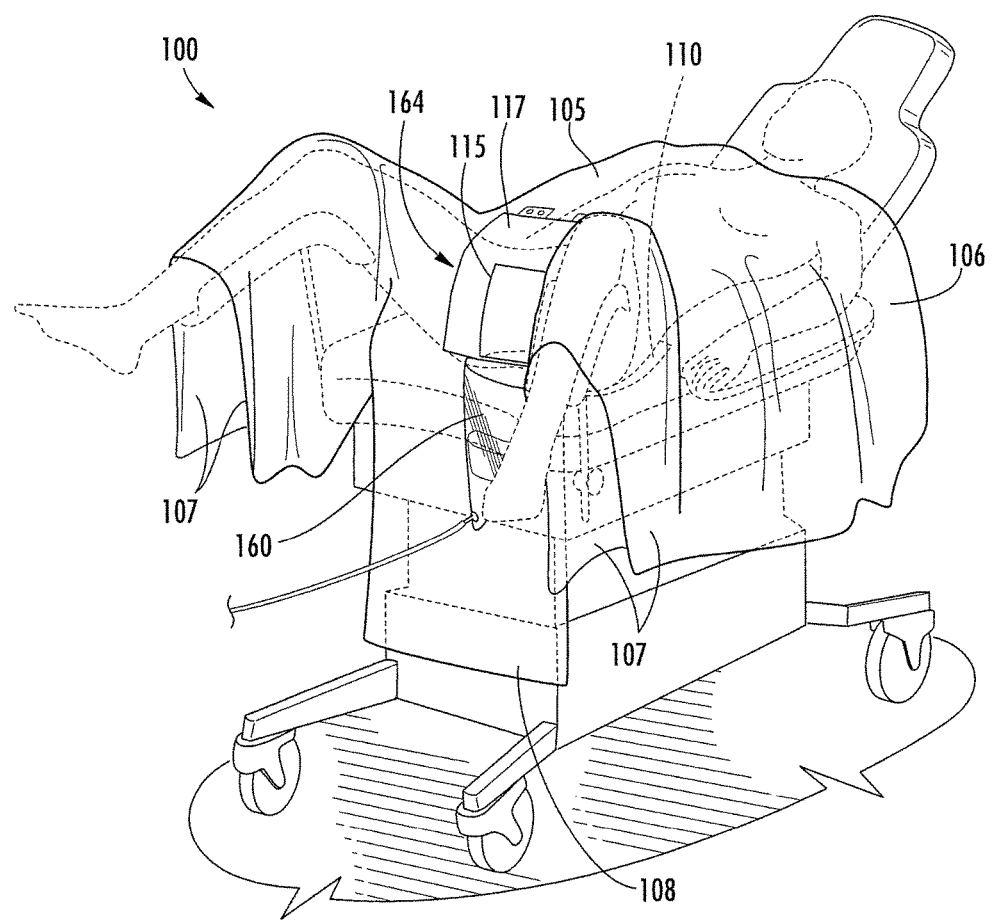
Figure 17:
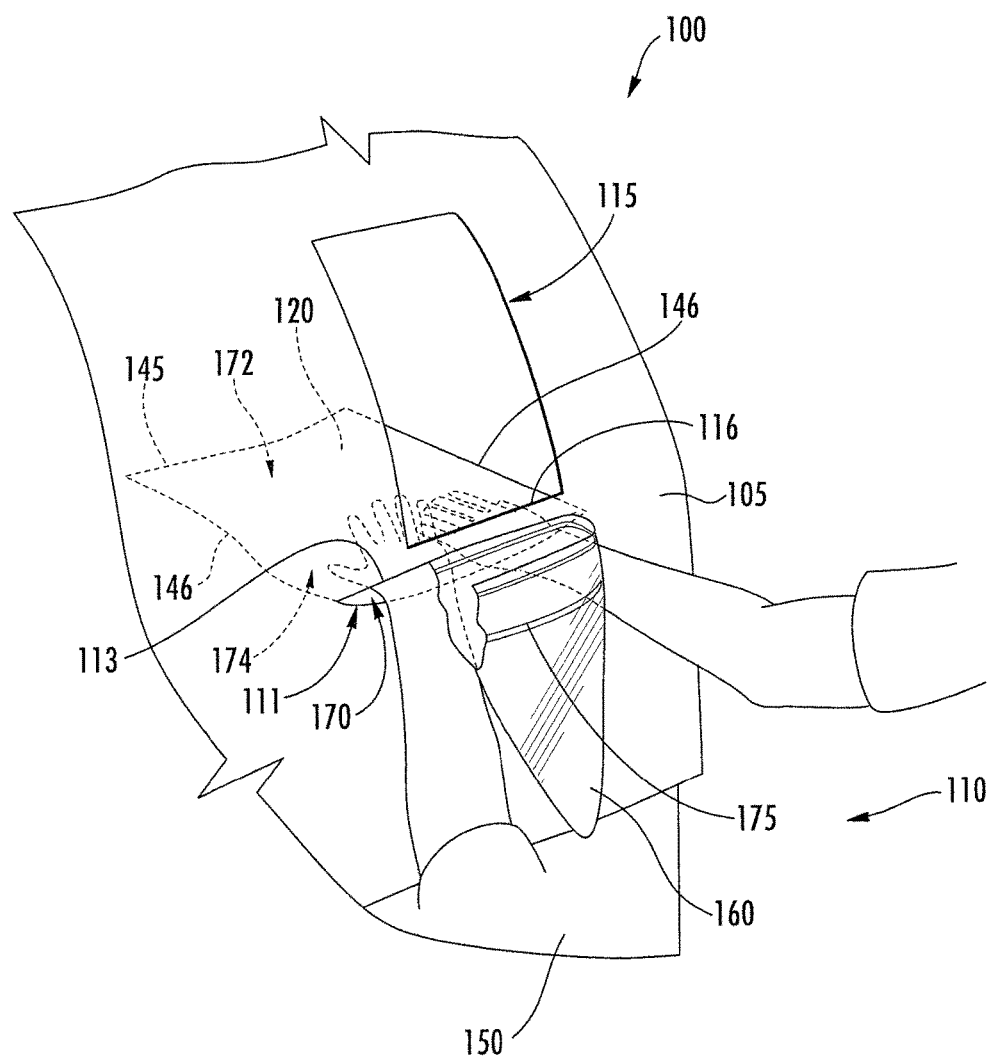

Having thus described the invention in general terms, reference will now be made to the accompanying drawings, which are not necessarily drawn to scale, and wherein:

FIG. 1 shows a conventional surgical drape covering a patient;

FIG. 2 shows a surgical drape covering a patient in accordance with an exemplary embodiment of the present invention;

FIG. 3 illustrates a view of the surgical drape of FIG. 2 from the position of the surgeon in accordance with an exemplary embodiment of the present invention;

FIG. 4 illustrates a side view cross-section of the surgical drape of FIG. 3 in accordance with an exemplary embodiment of the present invention;

FIG. 5 illustrates a perspective view of the collection pouch and collection portion of the surgical drape of FIG. 2 with the cover portion removed for purposes of explanation in accordance with an exemplary embodiment of the present invention;

FIG. 5A illustrates a close-up view of the edges of the main panel and a side panel of the collection portion of the surgical drape of FIG. 5;

FIG. 6 shows a simplified top plan view of the surgical drape lying on a flat surface in accordance with an exemplary embodiment of the present invention;

FIG. 7 illustrates a flowchart of a method for monitoring a distention fluid deficit level using a surgical drape in accordance with another exemplary embodiment of the present invention;

FIG. 8 illustrates a flowchart of a method for manufacturing a surgical drape in accordance with another exemplary embodiment of the present invention;

FIG. 9 shows a surgical drape covering a patient in accordance with another exemplary embodiment of the present invention;

FIG. 10 illustrates a view of the surgical drape of FIG. 9 from the position of the surgeon in accordance with an exemplary embodiment of the present invention;

FIG. 11 illustrates a side view cross-section of the surgical drape of FIG. 10 in accordance with an exemplary embodiment of the present invention;

FIG. 12 illustrates a side view cross-section of the surgical drape of FIG. 10 having a barrier strip in accordance with an exemplary embodiment of the present invention;

FIG. 13 illustrates a perspective view of the collection pouch and collection portion of the surgical drape of FIG. 9 with the cover portion removed for purposes of explanation in accordance with an exemplary embodiment of the present invention;

FIG. 14 shows a simplified top plan view of the surgical drape of FIG. 9 lying on a flat surface in accordance with an exemplary embodiment of the present invention;

FIGS. 15A and 15B illustrate a simplified perspective view of the collection portion of the surgical drape of FIG. 9 with portions removed for purposes of explanation to show how an operator may position the main panel in accordance with an exemplary embodiment of the present invention;

FIG. 16 shows a surgical drape covering a patient in accordance with another exemplary embodiment of the present invention; and FIG. 17 illustrates a simplified perspective view of the cover portion and the collection portion of FIG. 16 with parts removed for showing how a surgeon may access a pocket of the main panel via a slit formed in the cover portion.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, the terms "distal" and "distally" refer to a location farthest from the surgeon performing the medical procedure, and the terms "proximal" and "proximally" refer to a location closest to the surgeon performing the medical procedure. Furthermore, although each example described herein refers to distention of the uterine cavity during a hysteroscopy, embodiments of the described invention may be used to collect fluid other than or in addition to distending media and/or fluid discharged from other body cavities during other medical procedures.

As described above, conventional hysteroscopic procedures typically involve the introduction of distention fluid to expand the uterine cavity and allow the surgeon a better view of the uterine cavity. Turning to FIG. 1, for example, the patient 5 (shown in dashed lines) may be placed on an examining table 10 and positioned in a lithotomy position, as shown, such as through the use of stirrups. A conventional drape 15 may be placed over the patient's body 5 for the duration of the procedure. The conventional drape 15 typically includes an opening 20 that is positioned so as to allow surgical access to the patient's pelvic region. The drape 15 may include or be attached to a fluid collection pouch 30 that forms a trough for the purpose of collecting fluid that is discharged from the patient's uterine cavity.

In this regard, during a hysteroscopic procedure in which a conventional drape 15 is used, fluid discharged from the patient's uterus during insufflation is presumed to flow into the collection pouch 30, from which it is directed via a collection tube 35 for manual measurement or to a fluid management system that is configured to measure fluid inflow and outflow by weight so as to provide real-time, accurate monitoring of fluid deficit. The fluid deficit that is measured (e.g., the difference between the fluid inflow to and the fluid outflow from the uterus) is considered fluid that has been absorbed by the patient's uterine wall. Thus, as fluid deficit levels approach an upper limit of what is considered to be "safe" for the patient, the surgeon is alerted so that he or she may stop the hysteroscopic procedure to avoid additional fluid absorption by the patient (e.g., to avoid the risk of excessive fluid intravasation, intravascular fluid overload, and/or pulmonary complications).

Often, however, the level of fluid deficit, although accurately measured manually or by the fluid management system, does not correspond to the amount of fluid that has actually been absorbed by the patient's body. This is because some of the fluid discharged from the patient's uterus flows out of the cervix and vagina and is not collected by the collection pouch 30. Rather, some fluid may be soaked up by towels or blankets that may be provided under the patient's body (e.g., between the patient's body and the examining table surface 25) or may spill onto the floor 40. Such misdirected fluid is not considered in the inflow-outflow calculation.

As a result, a surgeon may be instructed (e.g., by the fluid management system) to stop a hysteroscopic procedure prematurely when there are indications that the patient is approaching an absorption limit (e.g., when the fluid deficit level, as calculated, is at or near a threshold level). If the surgeon abides by the warnings and stops the procedure prematurely, the procedure may be incomplete, which may adversely affect the outcome of the procedure and cause unnecessary discomfort to the patient and/or require repeat procedures to be performed. If the surgeon does not abide by the warnings (e.g., if the surgeon believes some of the fluid discharged is not being collected or considered and that the patient is, in fact not close to the threshold fluid absorption level) and continues the procedure, there is a risk that the patient may be put in danger of suffering from excessive fluid intravasation and fluid over-absorption.

Embodiments of the present invention are thus aimed at providing a way to direct a maximum amount of the fluid discharged from the patient's uterine cavity to a collection point, such as a downstream fluid management system. Turning to FIGS. 2-6 and 9-15B, embodiments of a surgical drape 100 are shown that include a cover portion 105 and a collection portion 110 that is attached to the cover portion and is placed under and behind the patient's buttocks, as described below. The cover portion 105 may define an opening 115 that is configured to provide a surgeon with surgical access to a patient for performing a medical procedure, such as access to the pelvic region for performing a hysteroscopy.

According to one embodiment shown in greater detail in FIGS. 3, 4, and 5, the collection portion 110 may include a main panel 120 extending between two side panels 125, 126.

The main panel 120 may be configured to be disposed under the patient's buttocks 130 in a first nominal plane P1, whereas each side panel 125, 126 may be arranged in a second nominal plane P2, P2' that is at an angle with respect to the first nominal plane so as to form a trough 135 for directing fluid discharged from the patient to a collection point 140. The main panel 120 may be arranged so as to minimize fluid loss from fluid flowing distally of (away from) the collection point 140, whereas the side panels 125, 126 may be configured and arranged to minimize lateral fluid loss. In this way, fluid discharged from the patient's uterine cavity via the cervix and vagina may be funneled and encouraged to flow towards the collection point 140, rather than being dispersed and soaking into any materials on which the patient is lying or falling onto the floor.

In particular, a distal edge 145 of the main panel 120 may be configured to be attached an underside of the patient's body distally of the gluteal cleft to the level of the lower back. For example, the distal edge 145 of the main panel 120 may include an adhesive strip 147. In such embodiments, as the patient is being positioned on the examining table 150, the adhesive strip 147 may be exposed (e.g., by peeling off a film layer 149 covering the adhesive strip 147, as shown in FIG. 5A), and the distal edge 145 carrying the adhesive strip may be pressed to the patient's skin to hold the main panel 120 in place. In some embodiments, the adhesive strip 147 may extend continuously along the length of the distal edge 145. In other embodiments, multiple adhesive patches may be provided along the distal edge 145. In still other embodiments, side edges 146 (shown in FIG. 5) and other portions (e.g., a central region) of the main panel 120 may also be provided with an adhesive strip or patches, such that the side edges may also be pressed and adhered to the patient's buttocks.

With continued reference to FIGS. 3, 4, and 5, the side panels 125, 126 may be configured to be attached to a corresponding thigh of the patient in some embodiments. For example, at least a portion of a lateral edge 155 of each side panel 125, 126 may be configured to be attached to an inner surface of the patient's thigh, so as to form the trough 135 when the patient is in the lithotomy position (as depicted in the figures). As described above with respect to the main panel 120, the portion of the lateral edge 155 of each side panel 125, 126 may comprise an adhesive strip to aid in the respective side panel being secured to the patient's thighs, as shown in FIG. 5A. Moreover, additional adhesive strips may be provided along other sides and portions of the side panels 125, 126 (e.g., in a central region of the side panels) to facilitate the attachment of the panels to the patient's skin.

Although the depicted embodiments include an adhesive strip on portions of the main panel 120 and/or the side panels 125, 126, the main panel and side panels may be secured in place with respect to the patient in other ways, as well. For example, the panels may, in some cases, be tied around a waist and/or thighs of the patient for securing them in place. Moreover, one or more portions of the main panel and/or side panels may include elastic or other materials that can be disposed around the patient's corresponding body part to hold the collection portion 110 in place.

Accordingly, in some embodiments, the collection portion 110 may define the distal edge 145, and the distal edge of the collection portion may be configured to be attached to the patient's body such that the trough 135 surrounds the patient's gluteal cleft and at least a portion of the patient's buttocks. In this way, fluid that may otherwise be directed via the gluteal cleft away from the collection portion 110 (e.g., toward the patient's back) may be re-directed by the main panel 120 and/or side panels 125, 126 toward the collection portion 110 and the collection point 140 to provide for a more accurate collection and measurement of the fluid discharge.

In some embodiments, the collection point 140 may comprise a collection pouch 160 that is configured to direct the fluid discharged from the patient to a collection system for measuring a volume of the fluid. The main panel 120 and/or the side panels 125, 126 may, in some cases, be continuous with the collection pouch 160 so as to funnel fluid into the collection pouch. The collection pouch 160 may, for example, include a mesh or filter 165 that is configured to separate out tissue or particles greater than a certain size that may be carried by the discharge so as to allow only the liquid part of the discharge to advance to the collection system for measurement and analysis. The collection system may, in some cases, be a fluid management system, such as a DOLPHIN® II Hysteroscopic Fluid Management System made by Gyrus ACMI of Southborough, Mass. In other cases, the fluid may be directed to a point downstream where it can be manually measured (e.g., by a nurse or technician).

To facilitate the funneling of liquid discharge from the patient to the collection point 140, the collection portion 110 may be integrally formed with the collection pouch 160. Alternatively, the collection pouch 160 may be separate from the collection portion 130 and may be deigned to be attached to the outer surface of the main panel 120 of the collection portion to secure the collection pouch 160 in place. In some embodiments, the collection portion 110 and/or the collection pouch 160 may be made at least partially of a hydrophobic material, such as a plastic material (e.g., polypropylene, etc.), to facilitate in directing the flow of discharge from the uterine cavity to the collection point 130 so as to allow for more accurate analysis and measurement. Moreover, in some cases, the plastic material of the collection portion 110 and/or the collection pouch 160 may be impregnated with an antimicrobial. In some cases, at least parts of the surgical drape 100 (e.g., the cover portion 105) may be made of nonwoven fabric, such as SMS fabric (spunbond+meltblown+spunbond fabric), in which two layers of spunbond material are combined with one layer of meltblown material to form the nonwoven fabric.

Alternatively or additionally, the collection pouch 160 may be designed such that the collection portion 110 may be attached to the cover portion 105 via the collection pouch. In this regard, as shown in FIGS. 2 and 3, a front edge 162 of the collection pouch 160 may extend towards and attach to an access panel 117 of the cover portion 105 at a connection interface 164. The collection portion 110, by virtue of its attachment to or being integral with the collection pouch 160, may thus be connected to the cover portion 105, such that the cover portion, collection pouch, and collection portion form a unitary surgical drape 100 in some embodiments. In some embodiments, the cover portion 105, the collection portion 110, the collection pouch 160, and/or the main panel 120 may be provided as separate pieces that can be attached to each other at the point of use to form the surgical drape 100, such as using an adhesive or via heat sealing. For example, in some cases, the operator, such as a surgeon, nurse, or technician, may assemble the surgical drape 100 from the separate pieces prior to using the drape in a procedure.

A simplified view of the surgical drape 100 laid out flat (e.g., laid out on a flat surface as opposed to covering a patient) is shown in FIG. 6. As depicted and described above, the surgical drape may include a cover portion 105, a collection pouch 160, and an underlying and attached collection portion 110 (e.g., attached via the collection pouch to the cover portion at first and second connection interfaces 164 as described above). Moreover, in some embodiments, the cover portion 105 itself may define a shape configured to aid in covering the patient's body when the patient is in a lithotomy position, as pictured in FIG. 2. For example, the cover portion 105 may include a main section 106 configured to cover a majority of the patient's body, two leg sections 107 configured to be draped over the patient's raised legs, and a front section 108 positioned behind the collection pouch 160 and configured to be draped over a front section of the examining table, between the patient's legs, as shown in FIG. 2.

Accordingly, embodiments of the surgical drape 100 may be used to allow a surgeon to more accurately monitor a distention fluid deficit level in a patient undergoing a hysteroscopy procedure. Turning to FIG. 7, for example, a method of monitoring a distention fluid deficit level in a patient undergoing a hysteroscopy is shown. According to embodiments of the method, the patient may be placed in a lithotomy position on an examining table at Block 200, such as through the use of stirrups, as shown in FIG. 2. A surgical drape, such as embodiments of the surgical drape described above with reference to FIGS. 2-6, may be placed over the patient at Block 210. The surgical drape may include a cover portion defining an opening and a collection portion attached to the cover portion, such that the cover portion covers the patient's body and the opening can be positioned to provide surgical access to the patient's pelvic region.

A main panel of the collection portion may be disposed under the patient's buttocks in a first nominal plane (e.g., the plane of the surface of the examining table) at Block 220. Furthermore, each of two side panels of the collection portion that extend from the main panel may be arranged such that each side panel is in a second nominal plane that is at an angle with respect to the first nominal plane at Block 230 so as to form a trough for directing distention fluid discharged from the patient to a collection point, as described above.

In some embodiments, disposing the main panel of the collection portion may include attaching a distal edge of the main panel to an underside of the patient's body distally of the gluteal cleft, so as to prevent distention fluid from being conducted by the gluteal cleft distally, toward the patient's back. In addition, arranging each of the two side panels may include attaching at least a portion of a lateral edge of each side panel to a corresponding thigh of the patient, so as to minimize or eliminate the amount of distention fluid that may flow outward and away from the collection point and, instead, redirect any such flow toward the collection point. In some embodiments, the distention fluid may be collected at the collection point via a collection pouch and directed to a collection system for measuring a volume of the fluid at Block 240.

Turning to FIG. 8, a method of manufacturing a surgical drape according to embodiments of the invention described above is provided. According to embodiments of the method, an opening may be defined in a cover portion at Block 300, where the opening is configured to provide surgical access to a patient. A collection portion may be formed comprising a main panel extending between two side panels at Block 310. The collection portion may be attached to the cover portion at first and second connection interfaces at Block 320, as described above. The main panel may thus be configured to be disposed under the patient's buttocks in a first nominal plane, and each side panel may be arranged in a second nominal plane that is at an angle with respect to the first nominal plane so as to form a trough for directing fluid discharged from the patient to a collection point.

In some embodiments, an adhesive strip may be disposed on a distal edge of the main panel at Block 330, such that the adhesive strip is configured to attach the distal edge of the main panel to the underside of the patient's body distally of the gluteal cleft as described above. In addition, an adhesive strip may be disposed on at least a portion of the lateral edge of each side panel at Block 340, such that the adhesive strip is configured to attach the respective portion to the patient's body (e.g., by attaching to the inner thigh, as described above). In some cases, a collection pouch may be provided proximate the collection point that is configured to direct the fluid to a collection system for measuring a volume of fluid. In this regard, the collection pouch may, in some embodiments, be integral to at least one of the main panel or the side panels of the collection portion.

Although in the embodiment described above and shown in FIGS. 2-6 a main panel 120 and side panels 125, 126 are provided to create a trough for directing the discharged fluid toward the collection point 140, in some embodiments a surgical drape is provided in which the collection portion includes a main panel in a single plane that is configured to direct fluid to the collection point, without the need for side panels. With reference to FIGS. 9-15B, for example, a surgical drape is provided that includes a cover portion 105 and a collection portion 110 that is attached to the cover portion and is placed under and behind the patient's buttocks, as described below. As described above with respect to the embodiments of FIGS. 2-6, the cover portion 105 may define an opening 115 that is configured to provide a surgeon with surgical access to a patient for performing a medical procedure, such as access to the pelvic region for performing a hysteroscopy.

As shown in FIGS. 9-11, for example, the collection portion 110 may comprise a collection pouch 160 and a main panel 120 extending from the collection pouch. The main panel may be configured to be disposed under the patient's buttocks 130 so as to direct fluid discharged from the patient to a collection point 140 via the collection pouch 160. In particular, a distal edge 145 of the main panel 120 may be configured to be attached an underside of the patient's body distally of the gluteal cleft to the level of the lower back. For example, the distal edge 145 of the main panel 120 may include an adhesive strip 147. In such embodiments, as the patient is being positioned on the examining table 150, the adhesive strip 147 may be exposed (e.g., by peeling off a film layer 149 covering the adhesive strip 147, as shown in FIG. 5A), and the distal edge 145 carrying the adhesive strip may be pressed to the patient's skin to hold the main panel 120 in place. In some embodiments, the adhesive strip 147 may extend continuously along the length of the distal edge 145. In other embodiments, multiple adhesive patches may be provided along the distal edge 145. In still other embodiments, side edges 146 (shown in FIG. 13) and other portions (e.g., a central region) of the main panel 120 may also be provided with an adhesive strip or patches, such that the side edges may also be pressed and adhered to the patient's buttocks and/or thighs.

Accordingly, in some embodiments, the collection portion 110 may define the distal edge 145, and the distal edge of the collection portion may be configured to be attached to the patient's body such that the main panel 120 surrounds the patient's gluteal cleft and at least a portion of the patient's buttocks 130. In this way, fluid that may otherwise be directed via the gluteal cleft away from the collection portion 110 (e.g., toward the patient's back) may be redirected by the main panel 120 toward the collection portion 110 and the collection point 140 to provide for a more accurate collection and measurement of the fluid discharge.

By way of comparison, in a conventional surgical drape 15, such as the one shown in FIG. 1, an attempt is made to collect fluid discharged from the patient in the fluid collection pouch 30 by adhering a portion of the drape forming the opening 20 to the perineal region of the patient, below the vaginal orifice. Such a configuration is less than ideal, however, as fluid discharged from the vaginal orifice typically trickles down into the perineal region and breaks the adhesive bond between the patient and the portion of the drape 15 near the opening 20. Once the adhesive bond, which may not have been very strong to begin with considering the curvature, clefts, skin texture, and/or hair on the patient's body interfering with formation of the bond, is broken, fluids in the conventional scenario typically run down the perineum, behind the drape, and are not taken into account by the collection system. Such fluid that is lost is improperly considered to be deficit, as noted above.

In contrast, however, embodiments of the surgical drape 100 shown in FIGS. 9 and 11 allow any fluid that runs down the patient's perineum to be deflected by the main panel 120 and funneled to the collection point 140.

In an effort to evaluate the effectiveness of the inventive drape in comparison to a conventional drape, the inventors conducted three comparative trials with the use of a pelvic model (gynecologic Simulator) in which a known amount of saline solution was introduced into the pelvic model and the outflow of saline solution was measured and recorded. Because no absorption of solution is possible using the pelvic model, the difference between the inflow amount and the outflow amount in each trial represented a loss, or deficit, of fluid.

For the conventional drape, a deficit of saline solution was recorded of between 340 ml and 820 ml, whereas no loss was observed in trials in which embodiments of the surgical drape 100 shown in FIG. 9 were used. The trials were conducted at a pressure of 50 mmHg and had a duration of 60 seconds, with approximately between 860 ml saline to 1260 ml saline flowing into the patient. Tables A and B below summarize the results of the trials for both the conventional drape 15 (Table A) and the embodiments of the improved surgical drape 100 (Table B).

TABLE A

Conventional Drape

Duration: 60 seconds
Pressure: 50 mmHg

| Trial No. | Saline Introduced (ml) | Loss (Deficit) (ml) |
| --- | --- | --- |
| 1 | 1250 | 340 |
| 2 | 862 | 482 |
| 3 | 1260 | 820 |

TABLE B

Inventive Drape

Duration: 60 seconds
Pressure: 50 mmHg

| Trial No. | Saline Introduced (ml) | Loss (Deficit) (ml) |
| --- | --- | --- |
| 1 | 1255 | 0 |
| 2 | 1059 | 0 |
| 3 | 1131 | 0 |

As noted above with respect to the embodiment shown in FIGS. 2-6, in the embodiments of FIGS. 9-15B, the collection point 140 may comprise a collection pouch 160 that is configured to direct the fluid discharged from the patient to a collection system for measuring a volume of the fluid. The main panel 120 may, in some cases, be continuous with the collection pouch 160 so as to funnel fluid into the collection pouch. To facilitate the funneling of liquid discharge from the patient to the collection point 140, the collection portion 110 may be integrally formed with the collection pouch 160. Alternatively, the collection pouch 160 may be separate from the collection portion 130 and may be deigned to be attached to the outer surface of the main panel 120 of the collection portion to secure the collection pouch 160 in place. In some embodiments, the collection portion 110 and/or the collection pouch 160 may be made at least partially of a hydrophobic material, such as a plastic material, to facilitate in directing the flow of discharge from the uterine cavity to the collection point 130 so as to allow for more accurate analysis and measurement.

Alternatively or additionally, the collection pouch 160 may be designed such that the collection portion 110 may be attached to the cover portion 105 via the collection pouch. In this regard, as shown in FIGS. 10 and 11, a front edge 162 of the collection pouch 160 may extend towards and attach to an access panel 117 of the cover portion 105 at a connection interface 164. The collection portion 110, by virtue of its attachment to or being integral with the collection pouch 160, may thus be connected to the cover portion 105, such that the cover portion, collection pouch, and collection portion form a unitary surgical drape 100 in some embodiments.

A simplified view of the surgical drape 100 laid out flat (e.g., laid out on a flat surface as opposed to covering a patient) is shown in FIG. 14. As depicted and described above, the surgical drape may include a cover portion 105, a collection pouch 160, and an underlying and attached collection portion 110 (e.g., attached via the collection pouch to the cover portion at first and second connection interfaces 164 as described above). Moreover, in some embodiments, the cover portion 105 itself may define a shape configured to aid in covering the patient's body when the patient is in a lithotomy position, as pictured in FIGS. 9 and 16 and described above. For example, the cover portion 105 may include a main section 106 configured to cover a majority of the patient's body, two leg sections 107 configured to be draped over the patient's raised legs, and a front section 108 positioned behind the collection pouch 160 and configured to be draped over a front section of the examining table, between the patient's legs, as shown in FIGS. 9 and 16.

In some embodiments, with reference to FIGS. 15A, 15B, and 17, the main panel 120 of the collection portion 110 may further comprise a pocket 170 proximate a distal edge 145 of the main panel. The pocket 170 may comprise, for example, a first wall 172 and a second wall 174, with the pocket 170 being formed therebetween. In some cases, for example, the distal edge 145 may be formed by an interface between the first and second walls 172, 174, which may, in some cases, be a fold line where a single sheet of material forming the main panel 120 is folded over to form the pocket 170 or where separate sheets of material forming the first and second walls 172, 174 are bonded or otherwise adhered together to form the pocket 170. The first and second walls 172, 174 may also be bonded or otherwise adhered together along their respective side edges 146 to form a pocket 170 that is closed on three sides.

Accordingly, in some embodiments, the pocket 170 may be configured to receive one or both hands of an operator, such as the surgeon, as shown, so as to facilitate the manipulation and placement of the collection portion 110 while maintaining a sterile condition of the operator. For example, as shown in FIGS. 15A and 17, the surgeon may place his or her hands in the pocket 170 when positioning the main panel 120 under the patient's buttocks 130, and the pocket may at the same time serve to maintain a sterile field by protecting the surgeon's hands and sleeves from any fluid or contamination from the patient's body.

For a surgical procedure, for example, a patient may be positioned on the examining table 150 after anesthesia has been administered and the patient's lower abdomen, perineum, and vaginal area have been prepped with antiseptic solution. The sterile surgical drape 100 may then be placed on the patient. In embodiments in which a pocket 170 is provided, the surgeon or other operator can wash his or her hands and put on a sterile gown and gloves, creating a sterile field, before the drape is applied and before the collection portion 110 is positioned. In this regard, the pocket 170, which may extend the full length of the main panel 120 as shown in some cases, can be used to maintain sterility during placement of the main panel under the patient's buttocks 130.

In FIG. 15A, for example, the operator (e.g., the surgeon) may have exposed the adhesive strips along the distal edge 145 and side edges 146 and may insert his or her hands into the pocket 170. As shown in FIG. 15B, other personnel in the operating room, such as nurses, technicians, or other doctors, may assist the operator by lifting up the patient's lower body (as depicted by the arrows) so that there is clearance between the patient's buttocks 130 and the examining table 150. The operator may then move the collection portion 110 into place under the patient's buttocks, as shown, using the pocket 170. Once the main panel 120 is in the appropriate location under the patient's buttocks 130, the operator may move his or her hand or hands within the pocket 170 to press along the adhesive strips to create an adhesive bond between the main panel and the patient's skin, attaching the collection portion 110 to the corresponding parts of the patient's buttocks and/or thighs. Once the main panel 120 is in place and adhered, the operator may withdraw his or her hand(s) from the pocket 170, leaving the collection portion 110 in the appropriate position for the procedure.

In other embodiments, such as embodiments in which the cover portion 105 of the surgical drape 100 extends downward between the patient's raised legs, the collection portion 110 may be attached to or otherwise integrally formed with the cover portion 105, such that the main panel 120 is disposed in one side of the cover portion and the collection pouch 160 is disposed on the other side of the cover portion. In this regard, as shown in FIG. 17, a slit 111 may be defined in the material of the cover portion 105, proximate a lower edge 116 of the opening 115. The slit 111 may extend a length configured to allow one or both of the operator's hands to pass through for accessing the pocket 170. For example, in some embodiments, the slit 111 may extend a length that is longer than the width of the lower edge 116 of the opening 115, as shown (e.g., approximately the width of the collection pouch 160 at the opening of the collection pouch). An upper edge 113 of the slit 111 may be connected (e.g., bonded or otherwise adhered) to a corresponding rear edge 161 of the opening of the collection pouch 160. In this way, the operator may be able access the pocket 170 of the main panel 120 by reaching behind the collection pouch 160, through the slit 111, and into the pocket 170 to position the main panel 120 appropriately beneath the patient, as described above with respect to FIG. 15B. At the same time, the operator's hands do not come into contact with the patient's body, and the sterile field that has been prepared for performing the procedure is maintained, as described above.

In some cases, a reinforcing member 175 may be provided proximate the opening of the collection pouch 160 to urge the collection pouch to maintain an open configuration for optimizing the collection of fluid therein. In some embodiments, for example, the reinforcing member 175 may be one or more strips of a malleable material that is attached to, embedded in, or otherwise integrated into the collection pouch 160. The reinforcing member 175 may, for example, be manipulated (e.g., bent) by the operator to achieve a desired size or shape of the opening of the collection pouch 160, such as to keep the collection pouch from collapsing or otherwise closing in on itself. In this regard, the reinforcing member 175 may extend approximately halfway around the collection pouch, as shown, or in other cases may extend less than halfway around (e.g., a quarter of the way around).

With reference now to FIG. 12, in some embodiments, the surgical drape 100 may further comprise a barrier strip 180 disposed proximate a distal edge 145 of the main panel 120. The barrier strip 180 may be configured to urge the distal edge towards contact with the patient's body so as to reduce a flow of the fluid discharged from the patient distally with respect to the barrier strip. For example, the barrier strip 180 may be configured to fit between the surface of the examining table 150 and the main panel 120 so as to urge the distal edge 145 of the main panel into further engagement with the patient's body, creating a more effective seal between the main panel material and the patient's skin. This may be particularly important when the distal edge 145 is placed in a location on the patient's body that may be unsupported by the examining table 150, such as near the small of the patient's back, or when the patient is in a position that encourages fluid to flow towards the patient's head, such as when the patient's pelvic region is raised with respect to the patient's head (e.g., in the Trendelenburg position).

In some embodiments, the barrier strip 180 may be integral to or attached to the main panel 120 proximate the distal edge 145, such as via adhesive or heat seal, such that the barrier strip forms part of the surgical drape 100. In other cases, the barrier strip 180 may be separate from the surgical drape 100 and may be positioned with respect to the patient before or after placement of the main panel 120, but separately from the positioning of the main panel 120. For example, embodiments of the invention may provide a kit that includes a surgical drape 100 as described above and a barrier strip 180 that is configured to be used in conjunction with the surgical drape.

The barrier strip 180 may, in some embodiments, be made of a spongy, resilient material, and in some cases the barrier strip may be made of foam, such as memory foam. Moreover, the barrier strip 180 may have numerous configurations. In some embodiments, the barrier strip 180 may have a triangular cross-section, as shown in FIG. 12, whereas in other embodiments, the barrier strip may have a circular cross-section, a square or rectangular cross-section, a trapezoidal cross-section, etc. In some cases, the barrier strip 180 may extend the entire length of the distal edge 145, whereas in other cases the barrier strip 180 may extend substantially the entire length of the distal edge or only a portion of the length of the distal edge, such as have the length of the distal edge along a central part of the main panel 120.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Moreover, it is understood that features of different embodiments described above may be used as features of other embodiments in different combinations. For examples, certain features of embodiments described above with respect to FIGS. 2-6 may be used in conjunction with or instead of certain features of embodiments described above with respect to FIGS. 9-15B. Although specific terms are employed herein, they are used in a generic and descriptive sense only and not for purposes of limitation.

What is claimed is:

1. A surgical drape comprising:
    a cover portion defining an opening configured to provide surgical access to a patient; and
    a collection portion attached to the cover portion, wherein the collection portion comprises a collection pouch and a main panel, wherein the main panel is integral with, attached or attachable to the collection pouch and extends from the collection pouch, below the cover portion,
    wherein the main panel is configured to be disposed under buttocks of the patient so as to direct fluid discharged from the patient to a collection point via the collection pouch, and wherein the main panel has a flexible planar body that is adapted to attach to and contact an underside of the patient,
    wherein the cover portion comprises an access panel segment that provides the opening configured to provide surgical access to the patient, wherein the access panel segment, in use, resides behind and above the collection pouch and above the main panel, and
    wherein the access panel segment is one of integral with, attached to or attachable to first and second connection interfaces of the collection pouch, the first connection interface residing on one side of the opening and the second connection interface residing on a laterally opposing side of the opening.

2. The surgical drape of claim 1, wherein a laterally extending distal edge of the main panel comprises at least one adhesive strip with a peelably releasable external layer, wherein the at least one adhesive strip is configured to be attached to the underside of the patient distally of a gluteal cleft.

3. The surgical drape of claim 2, wherein the main panel defines side edges, between which the distal edge extends, and wherein at least a portion of each side edge of the main panel comprises at least one adhesive strip with a peelably releasable external cover layer, and wherein the at least one adhesive strip is configured to be attached to a corresponding part of the underside of the patient.

4. The surgical drape of claim 1, wherein an upper surface of the main panel at a laterally extending distal edge portion and at first and second side edges each comprise at least one adhesive strip.

5. The surgical drape of claim 1, further comprising a barrier strip disposed under and proximate a laterally extending distal edge of the main panel configured to urge the distal edge towards contact with the underside of the patient so as to reduce a flow of the fluid discharged from the patient distally with respect to the barrier strip.

6. The surgical drape of claim 1, further comprising a reinforcing member disposed proximate an opening of the collection pouch, wherein the reinforcing member is configured to urge the collection pouch to maintain an open configuration, and wherein the reinforcing member extends laterally across an upper portion of the pouch.

7. The surgical drape of claim 1, wherein the collection portion is configured to collect distention fluid discharged from the patient.

8. A surgical drape comprising:
    a cover portion defining an opening configured to provide surgical access to a patient; and
    a collection portion attached to the cover portion, wherein the collection portion comprises a collection pouch and a main panel extending from the collection pouch,
    wherein the main panel is configured to be disposed under buttocks of the patient so as to direct fluid discharged from the patient to a collection point via the collection pouch,
    wherein the main panel comprises a pocket under an intact upper surface of the main panel, with a user access opening residing adjacent the collection pouch, and wherein the pocket is configured to receive at least one hand of an operator for allowing the operator to position the collection portion relative to the patient while maintaining a sterile field,
    wherein the cover portion comprises an access panel segment that provides the opening configured to provide surgical access to the patient, wherein the access panel segment, in use, resides behind and above the collection pouch and above the main panel, and
    wherein the access panel segment is one of integral with, attached to or attachable to first and second connection interfaces of the collection pouch, the first connection interface residing on one side of the opening and the second connection interface residing on a laterally opposing side of the opening.

9. The surgical drape of claim 8, wherein the main panel defines a slit as the pocket with the user access opening.

10. The surgical drape of claim 9, wherein the slit is proximate a lower edge of the opening of the cover portion.

11. The surgical drape of claim 8, wherein the pocket has a laterally extending slit that is the user access opening, wherein the slit has a laterally extending length that is greater than a laterally extending length of the opening of the cover portion, and in position, resides under the opening of the cover portion.

12. A method of monitoring a distention fluid deficit level in a patient undergoing a hysteroscopy comprising:
    positioning the patient in a lithotomy position;
    placing a surgical drape over the patient, wherein the surgical drape comprises a cover portion defining an opening and a collection portion attached to the cover portion, such that the cover portion covers the patient's body and the opening is positioned to provide surgical access to a pelvic region of the patient;
    disposing a main panel of the collection portion under buttocks of the patient such that distention fluid discharged from the patient is collected via a collection pouch of the collection portion; and
    adhesively attaching a planar body of the main panel to the patient,
    wherein the cover portion comprises an access panel segment that provides the opening configured to provide surgical access to the patient, wherein the access panel segment, in use, resides behind and above the collection pouch and above the main panel, and wherein the access panel segment is one of integral with, attached to or attachable to first and second connection interfaces of the collection pouch, the first connection interface residing on one side of the opening and the second connection interface residing on a laterally opposing side of the opening.

13. The method of claim 12, wherein the adhesively attaching comprises adhesively attaching at least a distal edge of the main panel to an underside of the patient, distally of a gluteal cleft.

14. The method of claim 13, further comprising allowing a user to slidably insert hands into a pocket defined by the main panel, wherein the pocket is configured to maintain a sterile field, and wherein the pocket is under an intact upper surface of the main panel, with a user access opening residing adjacent the collection pouch.

15. The method of claim 12, further comprising providing a malleable strip with sufficient rigidity to force the collection pouch to retain a bowl shape and directing the distention fluid in the collection pouch to a collection system for measuring a volume of the fluid.

16. A method of manufacturing a surgical drape comprising:
    defining an opening in a cover portion, wherein the opening is configured to provide surgical access to a patient;
    forming a collection portion comprising a main panel and a collection pouch configured to collect distention fluid discharged from the patient, wherein the main panel is configured to be disposed under buttocks of the patient so as to direct fluid discharged from the patient to the collection pouch; and
    disposing an adhesive strip on a distal edge portion of the main panel such that the adhesive strip is configured to attach the distal edge portion of the main panel to an underside of the patient distally of a gluteal cleft,
    wherein the cover portion comprises an access panel segment that provides the opening configured to provide surgical access to the patient, wherein the access panel segment, in use, resides behind and above the collection pouch and above the main panel, and
    wherein the access panel segment is one of integral with, attached to or attachable to first and second connection interfaces of the collection pouch, the first connection interface residing on one side of the opening and the second connection interface residing on a laterally opposing side of the opening.

17. The method of claim 16, wherein the adhesive strip comprises an outer peelably releasable cover layer.

18. The method of claim 16 further comprising defining a pocket accessible by a slit proximate a lower edge of the opening of the cover portion, wherein the pocket is under an intact upper surface of the main panel, adjacent the collection pouch.

19. The method of claim 18 further comprising connecting an upper edge of the slit to a corresponding rear edge portion of a wall segment providing an opening of the collection pouch at a location that is adjacent the opening of the collection pouch.

20. The method of claim 19 further comprising providing a reinforcing member proximate an opening of the collection pouch, wherein the reinforcing member is configured to urge the collection pouch to maintain an open configuration, and wherein the reinforcing member is malleable to allow a user to form a desired outwardly extending open configuration and extends laterally across an upper portion of the pouch.

21. A hysteroscopy surgical drape comprising:
    a cover portion defining an opening configured to provide surgical access to a patient; and
    a collection portion attached to the cover portion, wherein the collection portion comprises a collection pouch and a main panel extending from the collection pouch,
    wherein the main panel is configured to be disposed under buttocks of the patient so as to direct fluid discharged from the patient to a collection point via the collection pouch, and wherein the main panel has a flexible planar body that is adapted to attach to and contact an underside of the patient,
    wherein the main panel comprises a planar under buttocks portion with a laterally extending distal edge portion having at least one adhesive strip on an upper surface thereof, wherein the distal edge portion with the at least one adhesive strip is configured to releasably attach to the patient and has a lateral extent sufficient to extend across a gluteal cleft of the patient and at least part of buttocks of the patient,
    wherein the under buttocks portion merges into right and left side portions that adhesively attach to the buttocks or thighs of the patient to thereby create a wide fluid capture configuration to collect all fluid that flows laterally,
    wherein the main panel comprises a pocket under an intact upper surface of the buttocks portion that extends from a proximal edge with a user access opening to the distal edge portion whereby a user can insert at least one hand into the pocket via the user access opening and press upward adjacent the distal edge portion to attach the adhesive strip to the patient while maintaining sterility of the main panel,
    wherein the cover portion comprises an access panel segment that provides the opening configured to provide surgical access to the patient, wherein the access panel segment, in use, resides behind and above the collection pouch and above the main panel, and
    wherein the access panel segment is one of integral with, attached to or attachable to first and second connection interfaces of the collection pouch, the first connection interface residing on one side of the opening and the second connection interface residing on a laterally opposing side of the opening.

22. The surgical drape of claim 21, further comprising a malleable reinforcing member attached to and/or in the pouch which can be manipulated by a user to have a desired shape to place an upper portion of an outer wall of the pouch away from an inner wall thereof to maintain an open configuration of the pouch during use.

23. The surgical drape of claim 22, wherein the malleable reinforcing member comprises at least one laterally extending strip attached to the upper portion of the outer wall of the pouch.

* * * * *